United States Patent
Wolf, II

(10) Patent No.: US 9,550,063 B2
(45) Date of Patent: Jan. 24, 2017

(54) APPARATUS AND METHOD USING NEAR INFRARED REFLECTOMETRY TO REDUCE THE EFFECT OF POSITIONAL CHANGES DURING SPINAL CORD STIMULATION

(71) Applicant: Erich W. Wolf, II, Lake Charles, LA (US)

(72) Inventor: Erich W. Wolf, II, Lake Charles, LA (US)

(*) Notice: Subject to any disclaimer, the term of this patent is extended or adjusted under 35 U.S.C. 154(b) by 77 days.

(21) Appl. No.: 14/336,796

(22) Filed: Jul. 21, 2014

(65) Prior Publication Data
US 2014/0330341 A1 Nov. 6, 2014

Related U.S. Application Data

(63) Continuation-in-part of application No. 14/019,240, filed on Sep. 5, 2013, which is a continuation-in-part of
(Continued)

(51) Int. Cl.
*A61N 1/375* (2006.01)
*A61N 1/36* (2006.01)
(Continued)

(52) U.S. Cl.
CPC ......... *A61N 1/36071* (2013.01); *A61B 5/1116* (2013.01); *A61N 1/0551* (2013.01);
(Continued)

(58) Field of Classification Search
CPC .......... A61N 1/0551–1/0558; A61N 1/05; A61N 1/056–1/0565; A61N 1/3752
See application file for complete search history.

(56) References Cited

U.S. PATENT DOCUMENTS 5,076,270 A * 12/1991 Stutz, Jr. ............. A61N 1/3752
607/37
5,350,405 A 9/1994 Silvian
(Continued)

FOREIGN PATENT DOCUMENTS

WO 2007059362 5/2007

OTHER PUBLICATIONS

Philip, Geo M., et al., Fabrication of Negative Micro Axicons in Optical Fibers via Chemical Etching, ICOP 2009—International Conference on Optics and Photonics, Oct. 30, 2009, CSIO, Chandigarh, India.
(Continued)

*Primary Examiner* — George Evanisko
(74) *Attorney, Agent, or Firm* — Schultz & Associates, P.C.

(57) ABSTRACT

A positionally sensitive spinal cord stimulation apparatus and method using near-infrared (NIR) reflectometry are provided for automatic adjustments of spinal cord stimulation. The system comprises an electrode assembly with an integrated optical fiber sensor for sensing spinal cord position. The integrated optical fiber sensor, comprising a pair of optical elements for emitting light from an IR emitter and for collecting reflected light into a photodetector, determines a set of measured photocurrents. As the spinal cord changes position, the angles of incidence for light from the IR emitter and the measured optical intensities change. Electrode pulse characteristics are adjusted in real time, based on the set of measured optical intensities, to minimize changes in stimulation perceived by the patient during motion. The system includes automatic calibration of the optical fiber sensor when the patient is at rest, and a patient orientation detection.

11 Claims, 29 Drawing Sheets

Related U.S. Application Data application No. 13/780,470, filed on Feb. 28, 2013, now Pat. No. 9,132,273, which is a continuation-in-part of application No. 13/567,966, filed on Aug. 6, 2012, now Pat. No. 8,543,213, which is a continuation of application No. 12/925,231, filed on Oct. 14, 2010, now Pat. No. 8,239,038.

(60) Provisional application No. 61/867,413, filed on Aug. 19, 2013.

(51) Int. Cl.
*A61B 5/11* (2006.01)
*A61N 1/05* (2006.01)
*A61N 1/372* (2006.01)
*A61B 5/00* (2006.01)

(52) U.S. Cl.
CPC ..... *A61N 1/36139* (2013.01); *A61N 1/36157* (2013.01); *A61B 5/4836* (2013.01); *A61B 2562/0233* (2013.01); *A61N 1/36171* (2013.01); *A61N 1/36175* (2013.01); *A61N 1/37264* (2013.01)

(56) References Cited

U.S. PATENT DOCUMENTS

| | | | |
|---|---|---|---|
| 5,556,421 A | 9/1996 | Prutchi et al. | |
| 5,730,628 A * | 3/1998 | Hawkins | A61N 1/3752 439/843 |
| 5,824,021 A | 10/1998 | Rise | |
| 6,058,331 A | 5/2000 | King | |
| 6,120,467 A | 9/2000 | Schallhorn | |
| H1929 H | 12/2000 | Citak | |
| 6,169,924 B1 | 1/2001 | Meloy et al. | |
| 6,587,724 B2 | 7/2003 | Mann | |
| 6,622,048 B1 | 9/2003 | Mann et al. | |
| 6,871,099 B1 | 3/2005 | Whitehurst et al. | |
| 6,937,882 B2 | 8/2005 | Steuer et al. | |
| 7,127,296 B2 | 10/2006 | Bradley | |
| 7,162,304 B1 | 1/2007 | Bradley | |
| 7,216,000 B2 | 5/2007 | Sieracki et al. | |
| 7,263,402 B2 | 8/2007 | Thacker | |
| 7,330,762 B2 | 2/2008 | Boveja | |
| 7,333,857 B2 | 2/2008 | Campbell | |
| 7,359,751 B1 | 4/2008 | Erickson et al. | |
| 7,463,927 B1 | 12/2008 | Chaouat | |
| 7,539,543 B2 | 5/2009 | Schiff et al. | |
| 7,650,190 B2 | 1/2010 | Zhou et al. | |
| 7,684,869 B2 | 3/2010 | Bradley et al. | |
| 7,801,621 B1 | 9/2010 | Thacker et al. | |
| 7,805,197 B2 | 9/2010 | Bradley | |
| 8,165,676 B2 | 4/2012 | Donofrio | |
| 2003/0065366 A1 | 4/2003 | Merritt et al. | |
| 2003/0153959 A1 | 8/2003 | Thacker et al. | |
| 2005/0096720 A1 | 5/2005 | Sharma et al. | |
| 2005/0222628 A1 | 10/2005 | Krakousky | |
| 2006/0217793 A1* | 9/2006 | Costello | A61N 1/056 607/122 |
| 2007/0027514 A1 | 2/2007 | Gerber | |
| 2007/0100398 A1 | 5/2007 | Sloan | |
| 2007/0282403 A1 | 12/2007 | Tearney et al. | |
| 2008/0077190 A1* | 3/2008 | Kane | A61N 1/3752 607/37 |
| 2009/0118787 A1 | 5/2009 | Moffitt et al. | |
| 2009/0270960 A1 | 10/2009 | Zhao et al. | |
| 2010/0022861 A1 | 1/2010 | Cinbis et al. | |
| 2010/0105997 A1 | 4/2010 | Ecker et al. | |
| 2010/0106220 A1 | 4/2010 | Ecker et al. | |
| 2011/0029049 A1 | 2/2011 | Vertikov et al. | |
| 2015/0306414 A1* | 10/2015 | Nielsen | A61N 1/05 607/3 |

OTHER PUBLICATIONS

Utzinger, Urs, et al., Fiber Optic Probes for Biomedical Optical Spectroscopy, Feb. 2001, Tucson, Arizona.
Scott Prahl, Tabulated Molar Extinction Coefficient for Hemoglobin in Water, http://omlc.ogi.edu/spectra/hemoglobin/summary.html, Mar. 4, 1998, pp. 1-7.
Urs Utzinger, Oxygen saturation, http://www2.engr.arizona.edu/~bme517/supporting%20documents/PulseOximeter/Pulse%20OxiMeter%20Laboratory.htm#_Toc67647950, 2002, pp. 1-24.

* cited by examiner

FRONT, 0°

RIGHT, 90°

BACK, 180°

LEFT, 270°

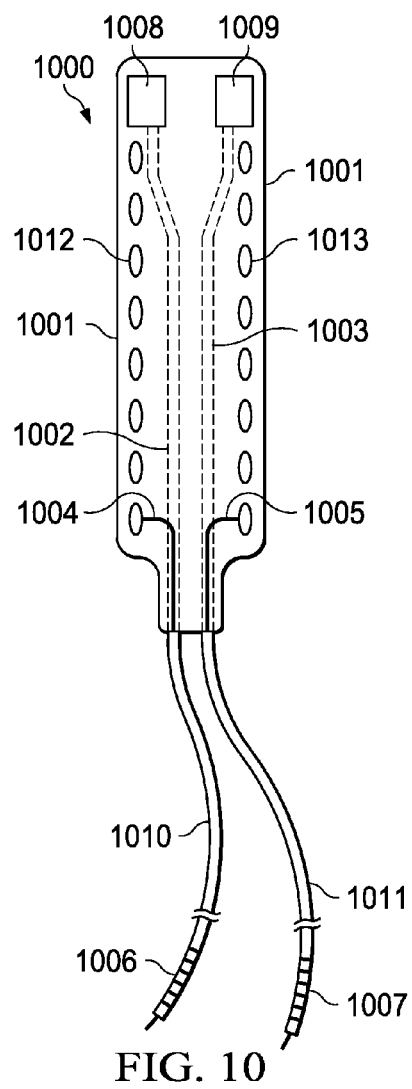
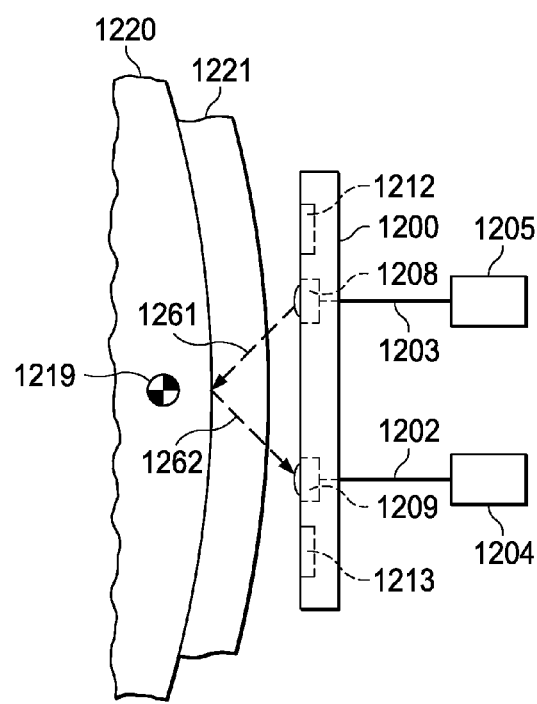
FIG. 10
FIG. 12

FRONT, 0°

RIGHT, 90°

BACK, 180°

LEFT, 270°

FRONT, 0°

RIGHT, 90°

BACK, 180°

LEFT, 270°

FIG. 24

| PATIENT POSITION | PATIENT ORIENTATION (ROLL, PITCH, YAW) | PHOTO-DETECTOR CURRENT | ELECTRODE PULSE AMPLITUDE | ELECTRODE PULSE WIDTH | ELECTRODE PULSE FREQUENCY |
|---|---|---|---|---|---|
| (FORWARD) - 0° | $R_1, P_1, Y_1$ | $PD_1$ | $A_1$ | $PW_1$ | $PF_1$ |
| (RIGHT) - 90° | $R_2, P_2, Y_2$ | $PD_2$ | $A_2$ | $PW_2$ | $PF_2$ |
| (BACK) - 180° | $R_3, P_3, Y_3$ | $PD_3$ | $A_3$ | $PW_3$ | $PF_3$ |
| (LEFT) - 270° | $R_4, P_4, Y_4$ | $PD_4$ | $A_4$ | $PW_4$ | $PF_4$ |

FIG. 25

| ROW INDEX | PATIENT POSITION | PHOTO-DETECTOR CURRENT MIN | PHOTO-DETECTOR CURRENT MAX | RIGHT ELECTRODE PULSE AMPLITUDE MIN | RIGHT ELECTRODE PULSE AMPLITUDE MAX | LEFT ELECTRODE PULSE AMPLITUDE MIN | LEFT ELECTRODE PULSE AMPLITUDE MAX |
|---|---|---|---|---|---|---|---|
| 1 | (FORWARD) 0° | $Pmin_1$ | $Pmax_1$ | $A_{RMin1}$ | $A_{RMax1}$ | $A_{LMin1}$ | $A_{LMax1}$ |
| 2 | (RIGHT) 90° | $Pmin_2$ | $Pmax_2$ | $A_{RMin2}$ | $A_{RMax2}$ | $A_{LMin2}$ | $A_{LMax2}$ |
| 3 | (BACK) 180° | $Pmin_3$ | $Pmax_3$ | $A_{RMin3}$ | $A_{RMax3}$ | $A_{LMin3}$ | $A_{LMax3}$ |
| 4 | (LEFT) 270° | $Pmin_4$ | $Pmax_4$ | $A_{RMin4}$ | $A_{RMax4}$ | $A_{LMin4}$ | $A_{LMax4}$ |

1

APPARATUS AND METHOD USING NEAR INFRARED REFLECTOMETRY TO REDUCE THE EFFECT OF POSITIONAL CHANGES DURING SPINAL CORD STIMULATION

CROSS-REFERENCE TO RELATED APPLICATIONS

This application is a Continuation-in-Part Application of U.S. patent application Ser. No. 14/019,240, filed Sep. 5, 2013, which is a Continuation-in-Part Application of U.S. patent application Ser. No. 13/780,470, filed Feb. 28, 2013, which is a Continuation-in-Part Application of U.S. patent application Ser. No. 13/567,966, filed Aug. 6, 2012, now U.S. Pat. No. 8,543,213, which is a continuation of U.S. patent application Ser. No. 12/925,231, filed Oct. 14, 2010, now U.S. Pat. No. 8,239,038. This application claims priority to U.S. Provisional Patent Application No. 61/867,413, filed Aug. 19, 2013. U.S. application Ser. No. 14/019,240 claims priority to U.S. Provisional Patent Application No. 61/867,413, filed Aug. 19, 2013. Each patent application identified above is incorporated here by reference in its entirety to provide continuity of disclosure.

FIELD OF DISCLOSURE

This disclosure relates generally to spinal cord stimulation (SCS) and technique for automatic adjustments of SCS using near-infrared (NIR) reflectometry.

BACKGROUND

Spinal cord stimulation is a technique which uses an implanted electrode array to control chronic pain. The electrode array is typically implanted in a fixed position within the epidural space near the spinal cord. A signal generator delivers current pulses to the spinal cord via the implanted electrode array. The current pulses help block the perception of pain.

In FIG. 1, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

In FIG. 2, representative vertebra 10, a thoracic vertebra, is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal.

Surrounding spinal cord 20 is dura 21 that contains cerebrospinal fluid (CSF) 22. Epidural space 24 is the space within the spinal canal lying outside the dura.

Referring to FIGS. 1, 2 and 3, the placement of an electrode array for spinal cord stimulation according to the prior art is shown. Electrode array 30 is positioned in epidural space 24 between dura 21 and the walls of spinal canal 16 towards the dorsal aspect of the spinal canal nearest bilateral laminae 15 and spinous process 17.

FIG. 4 shows a prior art electrode array 30 including electrode contacts 35 sealed into elastomeric housing 36. Electrode array 30 has electrode leads 31 which are connected to electrical pulse generator 32 and controller 33. The electrical pulse generator may be outside of the body or it may be implanted subcutaneously. Each electrode contact has a separate electrical conductor in electrode leads 31 so that the current to each contact may be independently controlled.

The anatomical distribution of parasthesias is dependent upon the spatial relationship between a stimulating electric field generated by the electrode array and the neuronal pathways within the spinal cord. The distribution may be changed by altering the current across one or more electrodes of the electrode array. Changing anode and cathode configurations of the electrode array also alters the distribution and hence, the anatomical pattern of the induced parasthesias.

Proper intensity of the current pulses is important. Excessive current produces an uncomfortable sensation. Insufficient current produces inadequate pain relief. Body motion, particularly bending and twisting, causes undesired and uncomfortable changes in stimulation due to motion of the spinal cord relative to the implanted electrode array.

There are methods and systems for controlling implanted devices within the human body. For example, Ecker et al, in U.S. Patent Publication No. 2010/0105997, discloses an implantable medical device that includes a controller and a plurality of sensor modules. A sensor includes at least one light source that emits light at a particular wavelength, which scatters through blood-perfused tissue a detector senses the light reflected by blood mass of a patient.

U.S. Pat. No. 7,684,869 to Bradley, et al. discloses a system using an interelectrode impedance to determine the relative orientation of a lead with respect to other leads in the spinal column. Bradley et al. further disclose that interelectrode impedance may be used to adjust stimulation energy.

U.S. Patent Publication No. 2009/0118787 to Moffitt, et al. discloses electrical energy conveyed between electrodes to create a stimulation region. Physiological information from the patient is acquired and analyzed to locate a locus of the stimulation region. The stimulation region is electronically displaced.

U.S. Pat. No. 7,413,474 to Liu, et al. discloses carbon nano-tube composites (see, for example, abstract, FIG. 2 and col. 3:11. 21-35). The disclosure of U.S. Pat. No. 7,413,474 is incorporated herein by reference.

Deficiencies exist in the prior art related to accuracy of spinal cord stimulation in relieving pain under changing circumstances. The deficiencies are most pronounced while the patient is moving. The prior art does not provide a satisfactory way to automatically adjust spinal cord stimulation to compensate for motion between the electrodes and the spinal cord to maintain a constant level of pain relief during patient motion.

SUMMARY

Embodiments of the present disclosure operate to automatically adjust spinal cord stimulation to compensate for patient movement. Automatic adjustment results in consistent parasthesias and conservation of battery power.

The disclosure demonstrates a novel optical sensor, generally useful in many fields of endeavor, in which a probe light beam is emitted from a first optical element and a responsive light beam is collected by a second optical element. In a preferred embodiment, the first optical element is coupled to the end of a first optical fiber and the second optical element is coupled to the end of a second optical fiber. The first optical fiber is further coupled to an active optical source. The second optical fiber is further coupled to an active optical detector.

Disclosed is a stimulator system having a surgical lead encasing the first and second optical fibers, electrode contacts and a controller. The optical source, operatively connected to the controller, generates an emitted light beam into the first optical fiber. The optical detector, also operatively connected to the controller, receives reflected light beams from the second optical fiber. Electrodes are operatively connected to the controller and the controller directs currents to the electrodes based on the reflected light beams.

In an aspect of the system, the reflected light beams are derived from the probe light beam as it interacts with the spinal cord of a host patient. In another aspect, the distance from surgical lead to the spinal cord is determined using optical reflectometry.

In another aspect of the system, the controller derives current pulse parameters for currents based on time averaging current pulse frequencies, time averaging current amplitudes, time averaging current pulse-widths, interpolating current pulse frequencies, interpolating current amplitudes and interpolating current pulse-widths.

In another aspect of the system, the controller includes an orientation detector and derives a real-time position of a host patient.

In a preferred embodiment, the system further comprises a calibration and programming unit operatively connected to the controller for calibrating the current pulse amplitudes, pulse widths and pulse frequencies. The current pulse amplitudes for the electrodes are calibrated to photocurrents derived from the optical detector while the patient is placed in different positions. Current pulse amplitude and values of photocurrents are stored in a calibration table corresponding patient position.

In another aspect, the controller is programmed to detect patient motion from photocurrents. When no motion has occurred for a predetermined time period, the controller recalibrates the optical source.

In another aspect the controller is programmed to detect patient orientation using an orientation sensor. When no change in orientation has occurred for a time period, the controller recalibrates the optical source.

BRIEF DESCRIPTION OF DRAWINGS

The following disclosure is understood best in association with the accompanying figures. Like components share like numbers.

FIG. 10 shows a preferred embodiment of a surgical lead.

FIG. 12 shows a cross-sectional axial view of a surgical lead.

FIG. 24 is a graphic representation of a preferred embodiment of a calibration table.

FIG. 25 is a graphic representation of a preferred embodiment of a calibration table.

DETAILED DESCRIPTION

Figures 1, 4:
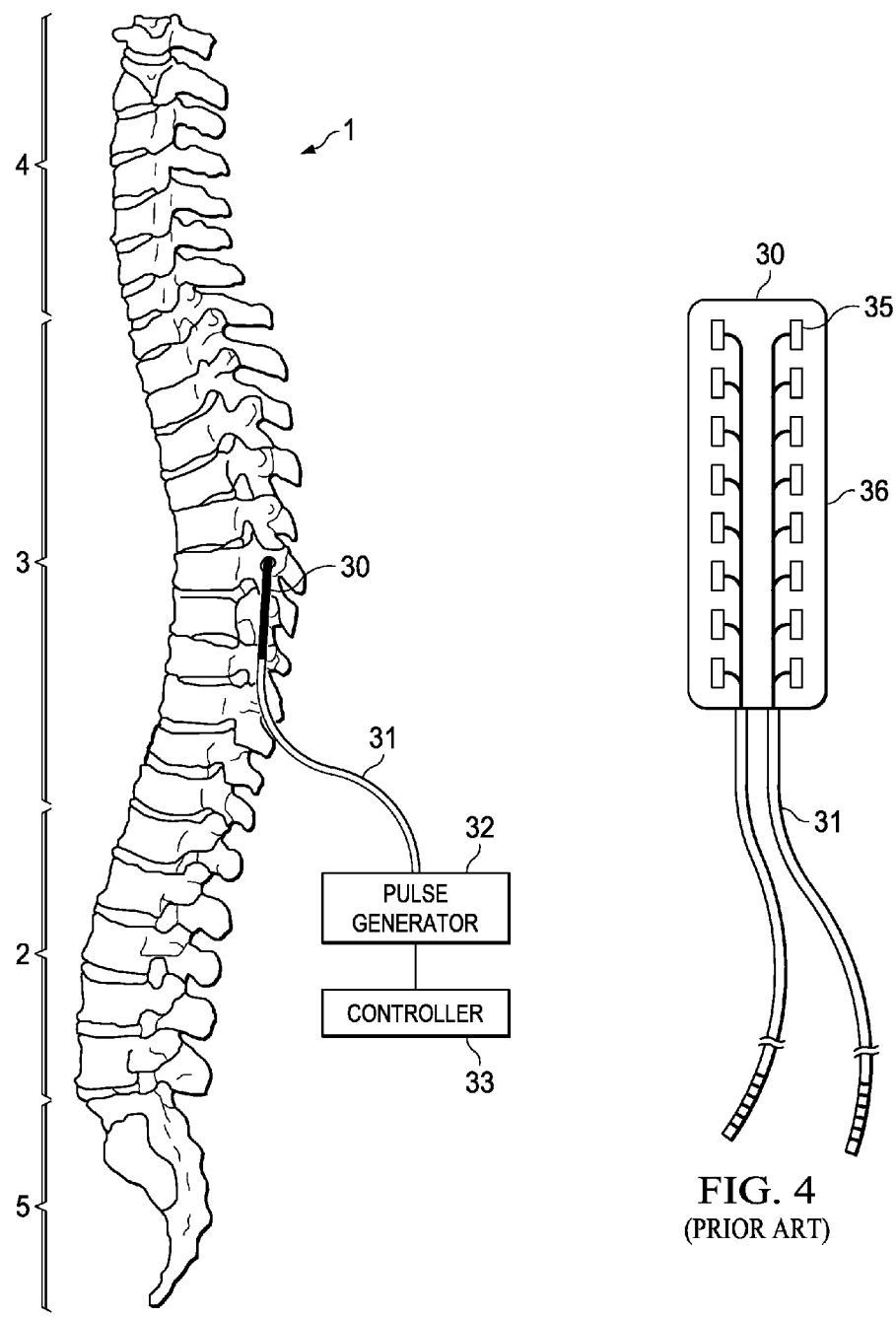
FIG. 1 shows a view of the human spine showing the various types of vertebrae and an approximate position of an electrode array for spinal cord stimulation.
FIG. 4 shows a prior art electrode array and a lead connector for spinal cord stimulation.
Figure 2:
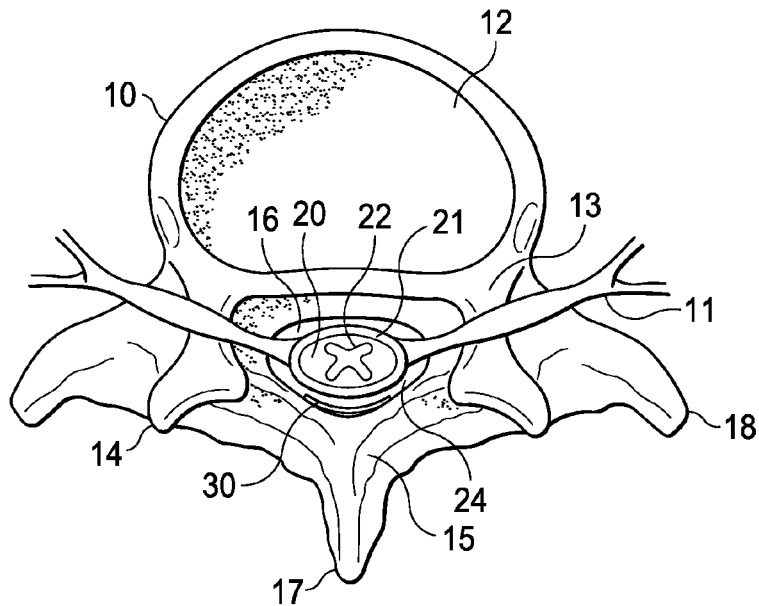
FIG. 2 shows an axial view of a thoracic vertebra indicating the position of the spinal cord and an electrode array for spinal cord stimulation.
Figure 3:
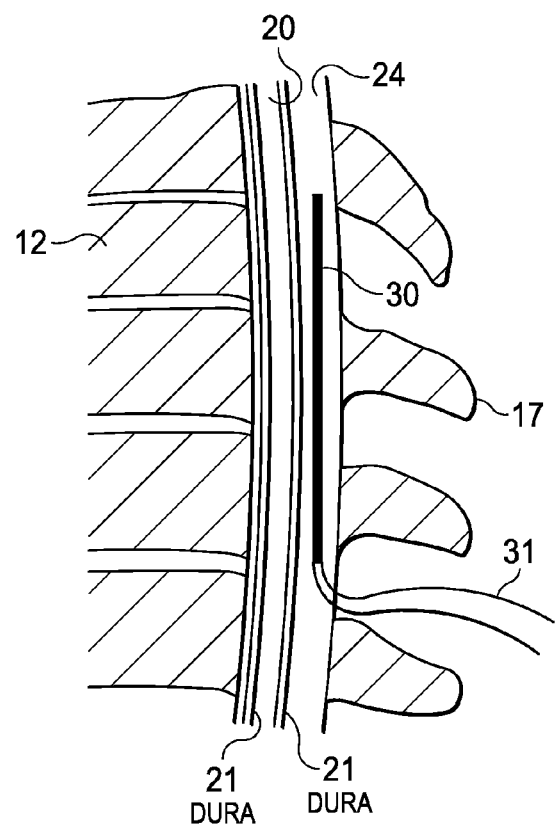
FIG. 3 shows a sagittal cross-sectional view of the human spine showing the approximate position of an electrode array for spinal cord stimulation.

The distance between a stimulating electrode and the spinal cord surface may be inferred from a function dependent upon: 1) the optical path lengths of light between a near infrared light emitter and detectors, where the light is reflected from the spinal cord; 2) the spinal cord geometry; 3) the optical divergence of the light emitter; and 4) the presence of chromophores in the optical path.

The dura surrounding the spinal cord itself is translucent to near infrared light. Near infrared light will be scattered by, and will reflect from, the spinal cord. Cerebrospinal fluid (CSF) will negligibly scatter near infrared light and will not act as a significant reflector of near-infrared light. Light from the light emitter passes through the thin, relatively avascular dura to enter the CSF. Light incident on the spinal cord experiences scatter resulting in a portion being reflected and another portion being absorbed by chromophores.

Optical absorption in a fluid medium may be described by the Beer-Lambert Law (Beer's Law), which is reasonably accurate for a range of chromophores and concentrations. Beer's Law states that the optical absorbance of a fluid with a chromophore concentration varies linearly with path length through the fluid and the chromophore concentration as:

$$A_\lambda = \epsilon_\lambda bc, \quad (\text{Eq. 1})$$

where:

$\epsilon_\lambda$ = molar absorptivity or extinction coefficient of the chromophore at wavelength $\lambda$ (the optical density of a 1-cm thick sample of a 1 M solution);

b = sample path length in centimeters; and, c = concentration of the compound in the sample, in molarity (mol $L^{-1}$).

The absorbance ($A_\lambda$) at a wavelength $\lambda$ is related to the ratio of light energy passing through the fluid, I, to the incident light energy, $I_0$, in $$A_\lambda = -\log(I/I_0). \quad (\text{Eq. 2})$$

For deoxyhemoglobin and oxyhemoglobin, the extinction coefficient spectra are well known.

The path length within the spinal cord is dependent upon the geometry of the ellipsoid shaped spinal cord cross-section and its normal vector relative to the optical axes of the emitter and detector pair.

The optical path length within CSF is roughly equal to the nominal geometric path length as the scatter is small and the index of refraction does not vary considerably along the path. Light absorption of the CSF may be approximated by that of its primary constituent, $H_2O$. Sensitivity of the system to CSF path length may be optimized using a light wavelength at a local maxima of the water extinction coefficient curve near 950-1100 nm.

When considering the light emitter wavelength, one must also consider the extinction coefficients of the primary chromophores, deoxy- and oxy-hemoglobin. To minimize effects of blood flow changes within the spinal cord (although these are thought to be insignificant in the quasi-static sense), one may select the isosbestic wavelength of these chromophore species, preferably at about 805 nm.

The geometry of the light emitter and detector aperture relative to the spinal cord is the parameter most prone to variability. The variance results from factors such as dependence upon placement of the electrode within the spinal canal, canal diameter, spinal cord shape, spinal cord caliber, and presence of scoliotic or kyphotic curvature within the spine. Consequently, this geometric parameter is the primary reason that the system must be calibrated, in situ, in vivo. Spinal cord position may then be inferred through various methods from data obtained at ordinal body positions.

The effects of geometry may be minimized by minimizing the angle between the light emitter and optical detector optical axes relative to the spinal cord surface normal vector.

The beam divergence of the light emitter relative to the incident and reflected rays will influence the detected light amplitude.

It is desirable to maintain a constant electric field at a group of target cells in the spinal cord as the spinal cord moves in order to consistently reduce the transmission of a pain sensation to the brain. With the patient in a prone position or bending forward (0° direction), the spinal cord moves anterior within its orbit in the spinal canal. An increase in stimulation pulse amplitude for each electrode pair is required to maintain the same electric field density. In the right lateral position or bent to the right (90° direction), the spinal cord moves to the right within its orbit in the spinal canal. A decrease in electrode stimulation pulse amplitude in the right electrode and an increase in electrode stimulation pulse amplitude in the left electrode of the electrode pair is required. In the supine position or bending backward (180° direction), the spinal cord moves dorsally within its orbit within the spinal canal. A decrease in electrode stimulation pulse amplitude bilaterally is required to maintain a constant electric field across the spinal cord. In the left lateral position or bent toward the left (270° direction), the spinal cord moves to the left within its orbit. A decrease in electrode stimulation pulse amplitude in the left electrode and an increase in electrode stimulation pulse amplitude in the right electrode of the electrode pair is required.

Figure 5A:
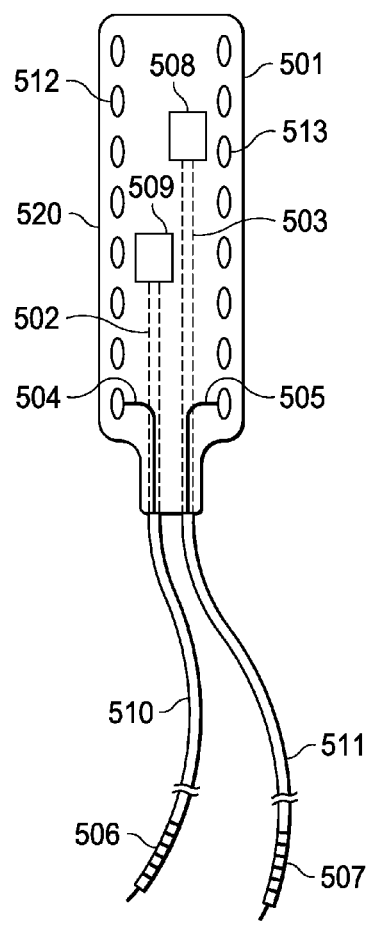
FIG. 5a shows a preferred embodiment of a surgical lead cable.

Referring to FIG. 5a, a preferred embodiment of surgical lead 520 is shown. Surgical lead 520 includes an elastomeric housing 501 connected to lead 510 and to lead 511. Optical fiber 502, optical fiber 503, electrodes 512 and electrodes 513 are embedded in elastomeric housing 501. In a preferred embodiment, the elastomeric housing is generally rectangular. Other shapes may suffice. Optical fiber 502 is terminated with optical element 509. Optical fiber 503 is terminated with optical element 508. Lead 510 encloses optical fiber 502 and wires 504 and is terminated with opto-electrical connector 506. Lead 511 encloses optical fiber 503 and wires 505 and is terminated with opto-electrical connector 507.

Figure 5B:
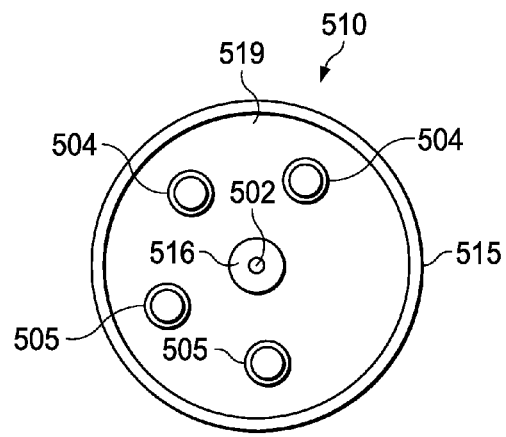
FIG. 5b shows a preferred embodiment of a surgical lead cable.

FIG. 5b shows a cross-sectional view of lead 510. Leads 510 and 511 are identical in structure. Lead 510 includes outer surface 515 which encapsulates wires 504, lumen 516 and filler material 519. Lumen 516 encloses optical fiber 502. Outer surface 515 is comprised of a shield for electromagnetic signals. In a preferred embodiment, the outer surface is made of a conductive material including metal sheeting, wire mesh and metal coatings. Filler material 519 is comprised of a polyimide polymer. In an alternate embodiment, filler material 519 can include additional materials with physical properties that enhance electromagnetic shielding properties such as conductive particles and/or carbon nano-tube composites.

Figure 5C:
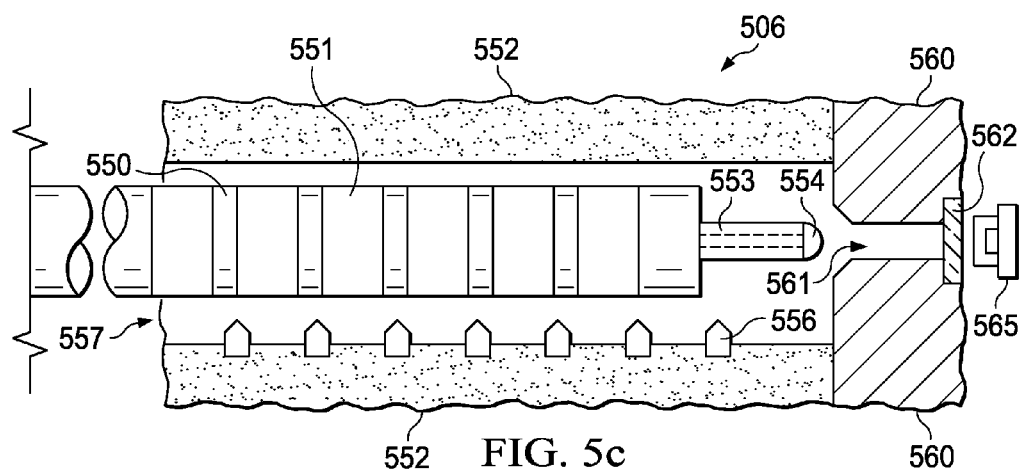
FIG. 5c is a cross-sectional view of a preferred embodiment of a connector.

Referring to FIG. 5c, opto-electrical coupler 506 is shown. Opto-electrical couplers 506 and 507 are identical in structure. In a preferred embodiment, opto-electrical coupler 506 includes case 560 with epoxy header 552, and optical fiber with cladding 553. Epoxy header 552 includes cavity 557. Cavity 557 includes spring loaded connectors 556 which are electrically connected to the pulse generator and sender unit (which will be further described). Case 560 includes cavity 561 connecting to cavity 557 and terminating in NIR transparent window 562. In a preferred embodiment, NIR transparent window 562 is flat. However, in an alternate embodiment, NIR transparent window is a lens. In another example, collimating lens 554 is an optical fiber with a polished end. Opto-electrical component 565 is situated behind the NIR transparent window. NIR transparent window 562 serves as a hermetic barrier between cavity 561 and opto-electrical component 565. NIR transparent window 562 also serves as an optical coupler. Opto-electrical component 565 may be an optical emitter. Opto-electrical component 565 may be an optical detector. In use, the lead is inserted into cavity 557 during a surgical procedure until collimating lens 554 is directly adjacent barrier 562. The spring connectors override and engage contacts 551 on lead 550.

Figure 6:
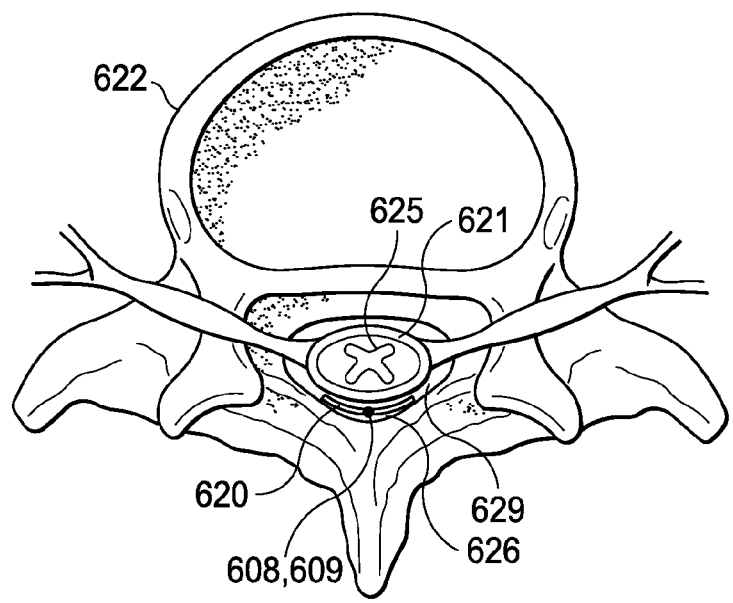
FIG. 6 shows a preferred placement of a preferred surgical lead in the spinal column.

FIG. 6 shows a cross-sectional view of a vertebra 622 and spinal cord 625. Surgical lead 620 is implanted in epidural space 626 of vertebra 622 between the dura 621 and the walls of the spinal canal 629 using a surgical procedure.

Figure 7:
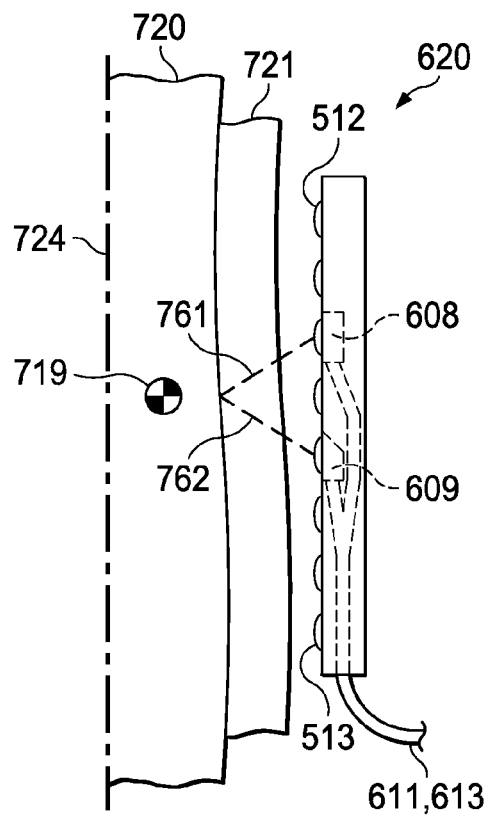
FIG. 7 shows a cross-sectional sagittal view of a surgical lead.

Referring to FIG. 7, a sagittal view of surgical lead 620 is shown implanted in relation to dura 721 and spinal cord 720. Spinal cord 720 includes target cells 719. Surgical lead 620 is implanted outside dura 721, approximately aligned with midline axis 724.

In use, probe light beam 761 is transmitted through optical fiber 611 and emitted from optical element 608. The probe light beam propagates through spinal canal, experiences absorption by the dura and the spinal fluid, and is reflected and scattered by the spinal cord. Reflected light beam 762 is collected by optical element 609 and is transmitted through optical fiber 613. Electrodes 512 and 513 supply stimulation current to the spinal cord based on the intensity of the reflected light beam.

Referring to FIGS. 8a-8d, axial views of the spinal cord 820 and surgical lead 800 are shown with spinal cord 820 and dura 821 in various positions in the spinal canal caused by movement of the patient. The figures are shown in relation to coronal axis 824 and sagittal axis 825.

Figure 8A:
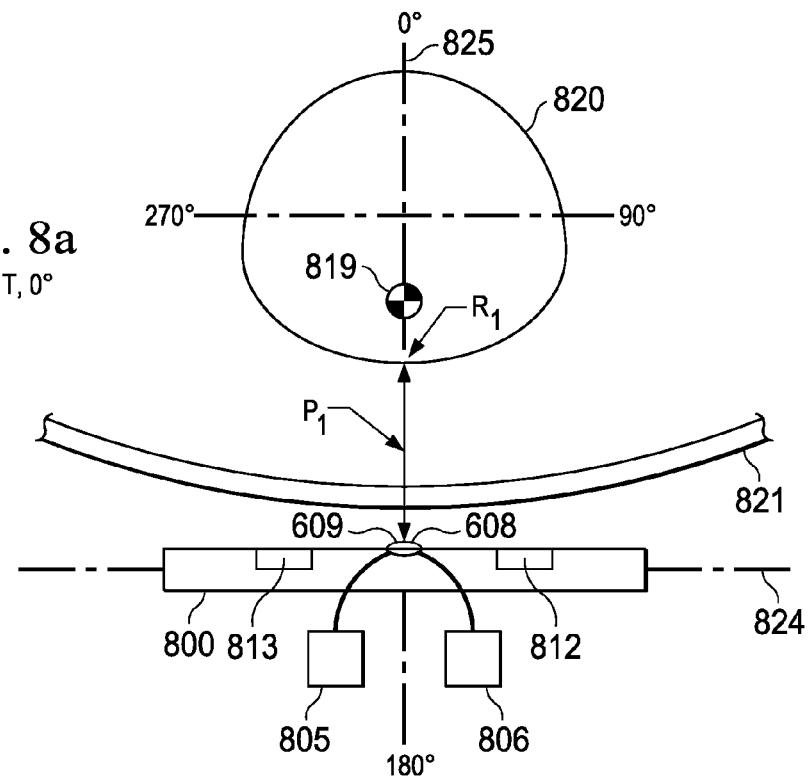
FIG. 8a shows a cross-sectional axial view of a surgical lead with a spinal cord at a forward position.

Referring to FIG. 8a, spinal cord 820 is in a forward position toward 0° along sagittal axis 825. Path $P_1$ defines a light path from optical element 608 to reflection point $R_1$ and then to optical element 609. The length of path $P_1$ is $D_1$. Optical element 608 emits light from optical source 805 along path $P_1$ where it is reflected at point $R_1$ by the spinal cord surface. Optical element 609 collects light from path $P_1$ after reflection at point $R_1$. Light collected by optical element 609, is detected by photodetector 806 and converted to photocurrent $I_1$ in response.

Figure 8B:
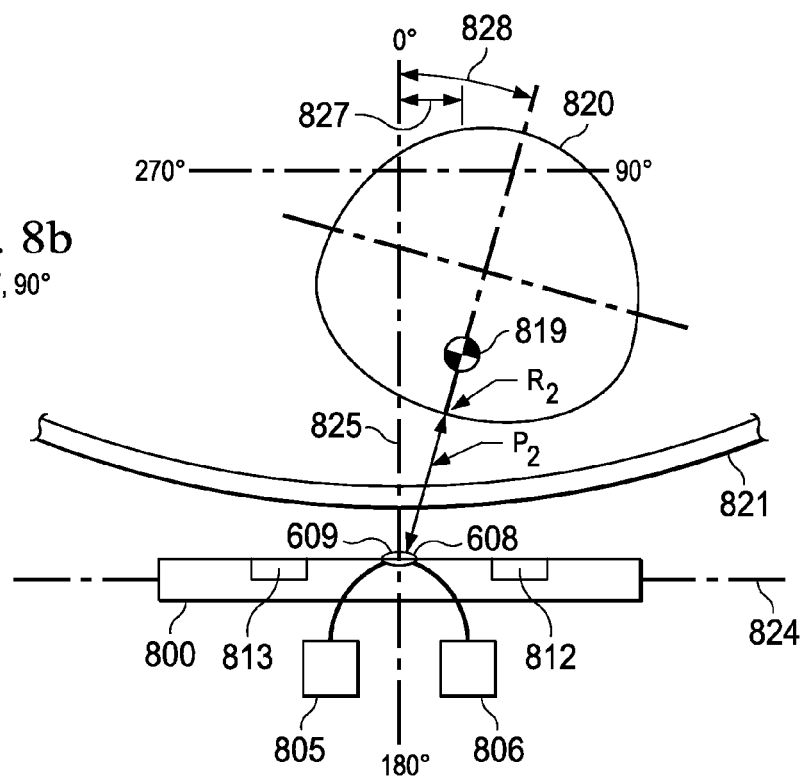
FIG. 8b shows a cross-sectional axial view of a surgical lead with a spinal cord at a rightward position.

In FIG. 8b, spinal cord 820 is in a rightward position, rotated by angle 828 from sagittal axis 825 where target cells 819 are shifted rightward toward 90° and parallel to coronal axis 824 by distance 827. Path $P_2$ defines a light path from optical element 608 to reflection point $R_2$ and then to optical element 609. The length of path $P_2$ is $D_2$ (which is less than $D_1$). Optical element 609 emits light from optical emitter 805 along path $P_2$ where it is reflected at point $R_2$ by the spinal cord surface. Optical element 608 collects light from path $P_2$ after reflection at point $R_2$. Light collected by optical element 608, is detected by photodetector 806 and converted to photocurrent $I_2$ in response.

Figure 8C:
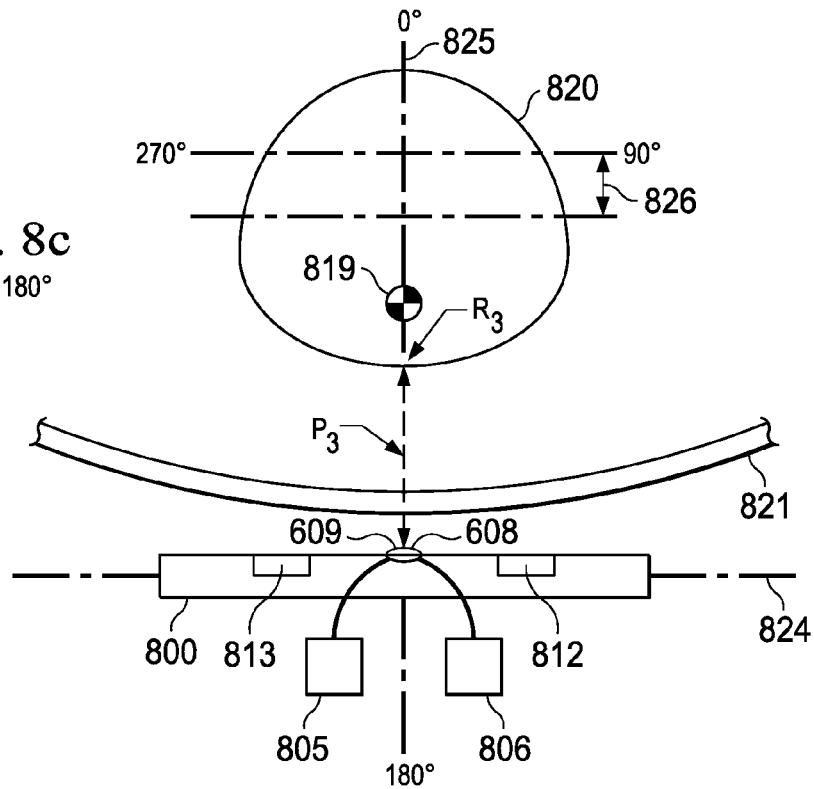
FIG. 8c shows a cross-sectional axial view of a surgical lead with a spinal cord at backward position.

In FIG. 8c, spinal cord 820 is in a posterior position shifted by a distance 826 towards optical elements 608 and 609 along sagittal axis 825. Path $P_3$ defines a light path from optical element 609 to reflection point $R_3$ and then to optical element 608. The length of path $P_3$ is $D_3$ (which is less than $D_1$ or $D_2$). Optical element 609 emits light from optical emitter 805 along path $P_3$ where it is reflected at point $R_3$ by the spinal cord surface. Optical element 608 collects light from path $P_3$ after reflection at point $R_3$. Light collected by optical element 608, is detected by photodetector 806 and converted to photocurrent $I_3$ in response.

Figure 8D:
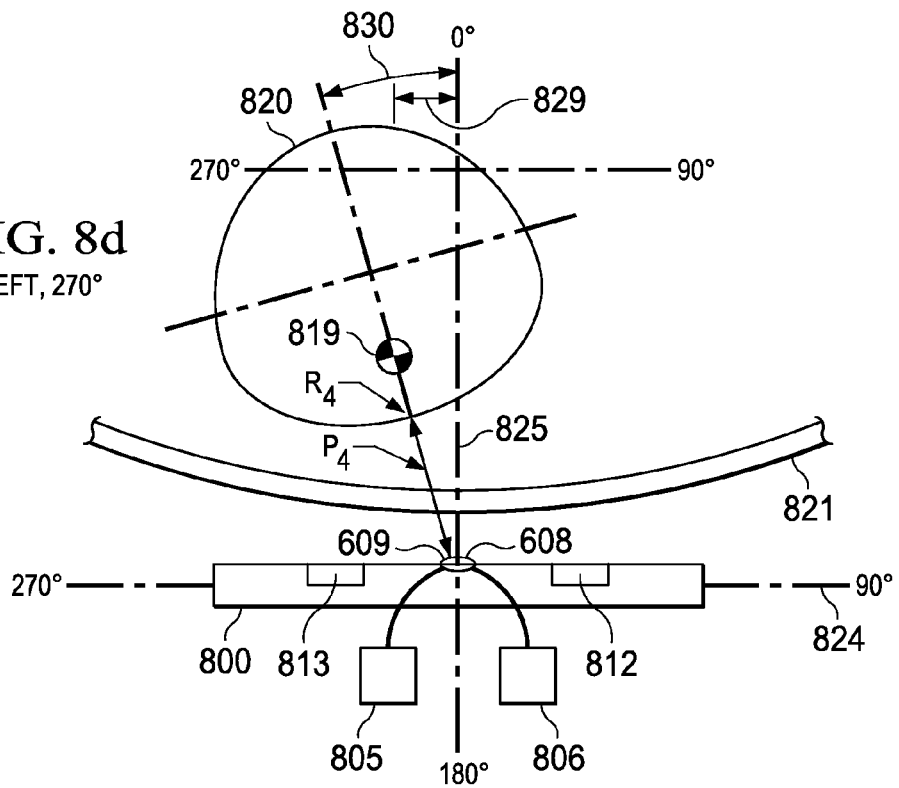
FIG. 8d shows a cross-sectional axial view of a surgical lead with a spinal cord at leftward position.

In FIG. 8d, spinal cord 820 is in a left position, rotated by angle 830 from sagittal axis 825 where target cells 819 are shifted leftward along sagittal axis 824 by distance 829. Path $P_4$ defines a light path from optical element 609 to reflection point $R_4$ and then to optical element 608. The length of path $P_4$ is $D_4$ which is less than $D_1$, but about the same as $D_2$. Optical element 609 emits light from optical emitter 805 along path $P_4$ where it is reflected at point $R_4$ by the spinal cord surface. Optical element 608 collects light from path $P_4$ after reflection at point $R_4$. Light collected by optical element 608, is detected by photodetector 806 and converted to photocurrent $I_4$ in response.

An electric field produced by the electrodes 801, including electrodes 812 and electrodes 813, stimulates target cells 819 in the spinal cord 820. Current amplitude is supplied to the electrodes in pulses, each having a pulse width and a pulse frequency. The relative current amplitude must be increased as the target cells move away from the electrodes. Also, the intensity of the reflected signal decreases as the surface of the spinal cord moves away from the optical elements. Hence, as the reflected light beam decreases, the current amplitude must increase to maintain the same electrical field intensity at the target cells.

Figure 9:
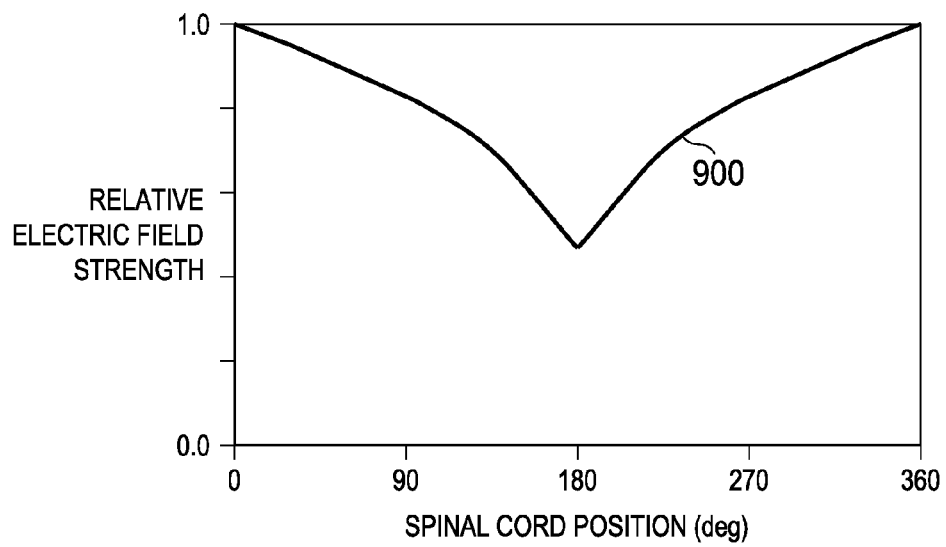
FIG. 9 shows the relative electric field produced by a preferred embodiment for the spinal cord in various positions within the spinal canal.

FIG. 9 shows a plot 900 of relative electric field strength required to be generated at the electrodes in order to maintain a constant electrical field at target cells 819, as the spinal cord is moved through an orbit of 360° in the spinal canal.

The foregoing results are tabulated in Table 1.

TABLE 1

| Position | Photodetector Current, I | Stimulation Current Amplitude, A |
|---|---|---|
| 1. Front 0° | Low | High |
| 2. Right 90° | Medium | Medium |
| 3. Back 180° | High | Low |
| 4. Left 270° | Medium | Medium |

Referring to FIG. 10, an alternate embodiment of a surgical lead is shown. Surgical lead 1000 includes an elastomeric housing 1001 connected to lead 1010 and to lead 1011. Embedded in elastomeric housing 1001, are optical fiber 1002, optical fiber 1003, electrodes 1012 and electrodes 1013. Optical fiber 1002 is terminated with an optical element 1008. Optical fiber 1003 is terminated with optical element 1009.

Lead 1010 encloses optical fiber 1002 and wires 1004 which are terminated in opto-electrical connector 1006. Lead 1011 encloses optical fiber 1003 and wires 1005 which are terminated in opto-electrical connector 1007.

Figure 11:
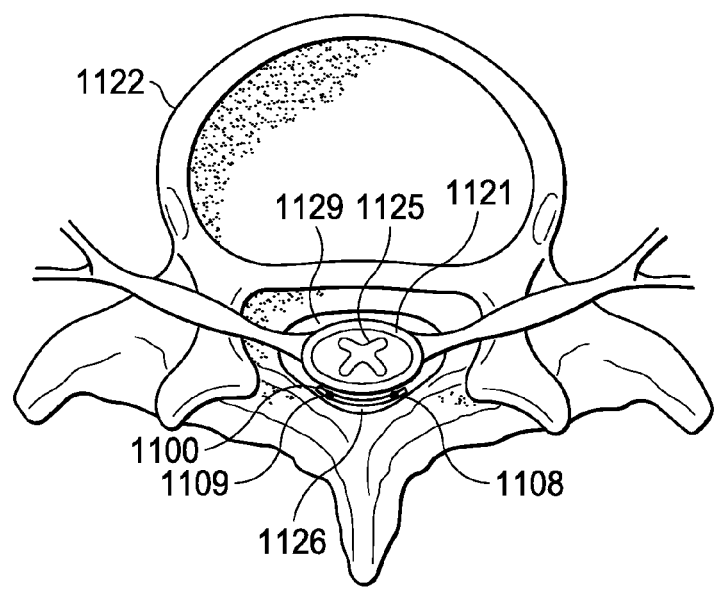
FIG. 11 shows a preferred placement of a surgical lead in a spinal column.

Referring to FIG. 11, a cross-sectional view of vertebra 1122 is shown enclosing spinal cord 1125. Surgical lead 1100 is placed in the epidural space 1126 of vertebra 1122 between dura 1121 and the walls of the spinal canal 1129. Surgical lead 1100 includes optical elements 1108 and 1109.

Referring to FIG. 12, a top view of surgical lead 1200 is shown implanted adjacent dura 1221. Optical source 1205 and optical detector 1204 are shown schematically. Surgical lead 1200 includes optical element 1208 coupled to optical source 1205 and optical element 1209 coupled to optical detector 1204. Surgical lead 1200 is positioned within an operational range of target cells 1219.

In use, light beam 1261 is emitted from optical source 1205, propagates through optical fiber 1203 and exits from optical element 1208. The light beam then propagates through spinal canal, experiences absorption by the dura and the spinal fluid, and is reflected and scattered by the surface of the spinal cord. Reflected light beam 1262 is collected by optical element 1209. Reflected light beam 1262 propagates through optical fiber 1202 and is detected by optical detector 1204.

Referring to FIGS. 13a-13d, top views of spinal cord 1220 and surgical lead 1200 are shown with spinal cord 1220 in various positions. Electrodes 1212 and 1213 supply stimulation current to the spinal cord. Surgical lead 1200 is approximately aligned with coronal axis 1324. The figures are shown in relation to coronal axis 1324 and sagittal axis 1325.

Figure 13A:
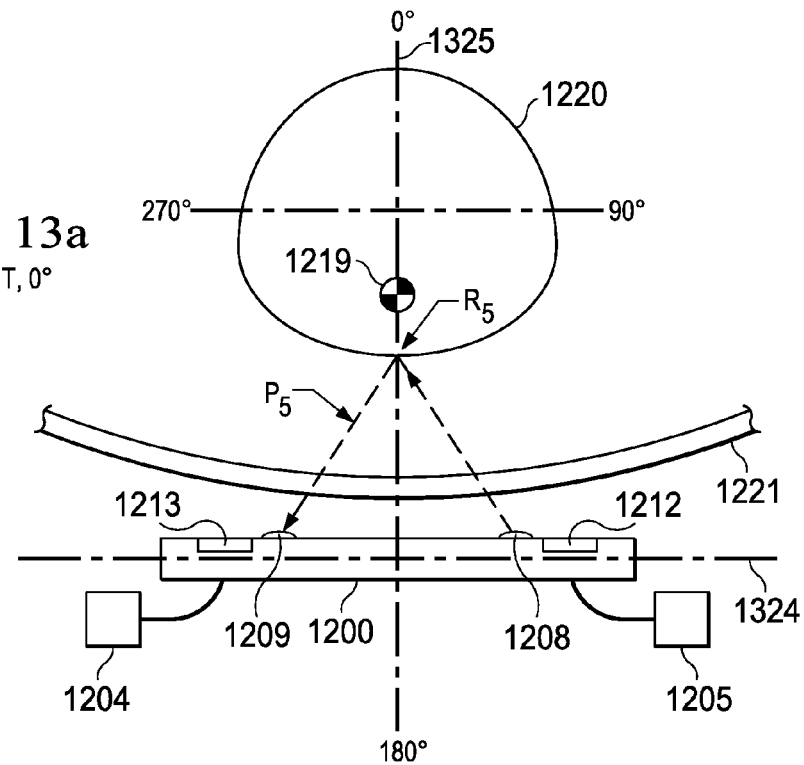
FIG. 13a shows a cross-sectional axial view of a surgical lead located in relation to a spinal cord at a forward position.

Referring to FIG. 13a, the spinal cord is positioned forward. Path $P_5$ defines a light path from optical element 1208 to reflection point $R_5$ and then to optical element 1209. The length of path $P_5$ is $D_5$. Optical element 1208 emits light along path $P_5$ and optical element 1209 collects light from path $P_5$ after reflection at point $R_5$ from spinal cord 1220. Light collected by optical element 1209 is detected by photodetector 1204 which produces a photocurrent of $I_5$ in response.

Figure 13B:
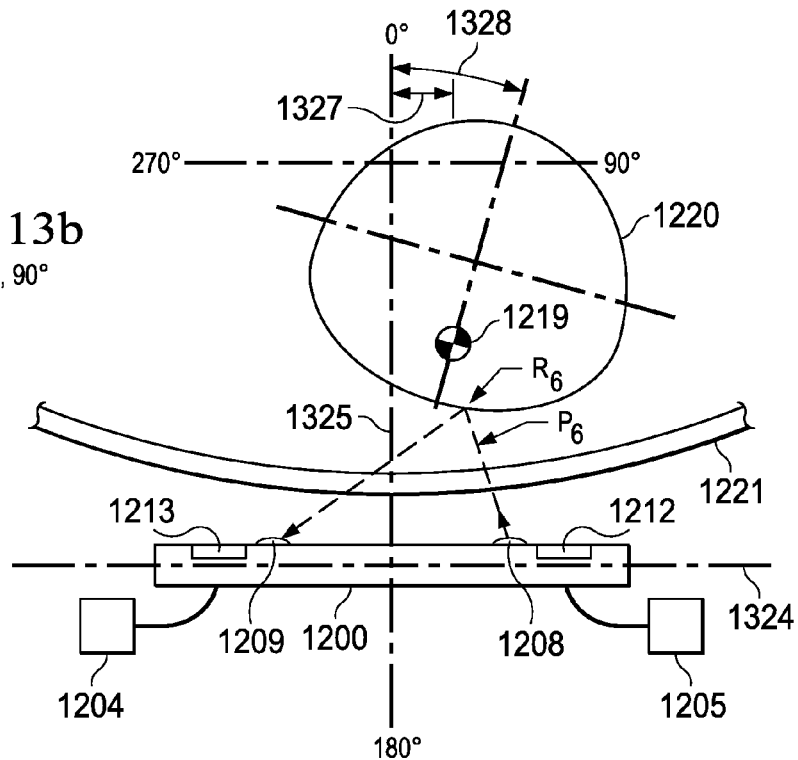
FIG. 13b shows a cross-sectional axial view of a surgical lead located in relation to a spinal cord at a rightward position.

Referring to FIG. 13b, the spinal cord is rotated through angle 1328 and positioned rightward by a distance 1327. Path $P_6$ defines a light path from optical element 1208 to reflection point $R_6$ and then to optical element 1209. The length of path $P_6$ is $D_6$ which is less than the length $D_5$. Optical element 1208 emits light along path $P_6$ and optical element 1209 collects light from path $P_6$ after reflection at point $R_6$ from spinal cord 1220. Light collected by optical element 1209 is detected by photodetector 1204 which produces a photocurrent of $I_6$ in response. $I_6$ is greater than $I_5$.

Figure 13C:
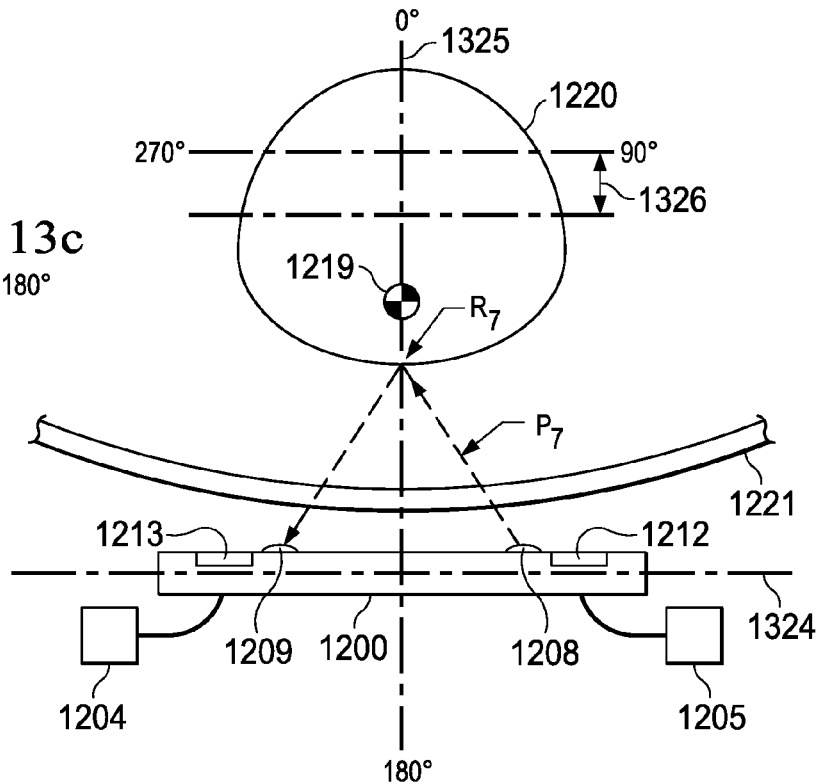
FIG. 13c shows a cross-sectional axial view of a surgical lead located in relation to a spinal cord at a backward position.

Referring to FIG. 13c, the spinal cord is positioned towards the back and displaced by a distance 1326. Path $P_7$ defines a light path from optical element 1208 to reflection point $R_7$ and then to optical element 1209. The length of path $P_7$ is $D_7$ which is shorter than length $D_5$ or $D_6$. Optical element 1208 emits light along path $P_7$ and optical element 1209 collects light from path $P_7$ after reflection at point $R_7$ from spinal cord 1220. Light collected by optical element 1209 is detected by photodetector 1204 which produces a photocurrent of $I_7$ in response. $I_7$ is greater than $I_5$ and $I_6$.

Figure 13D:
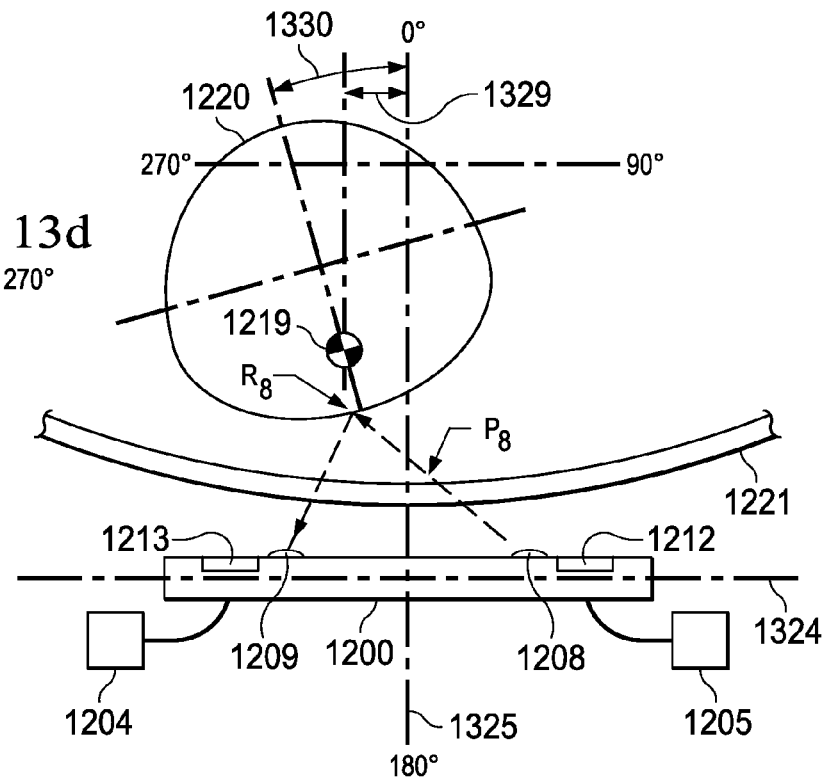
FIG. 13d shows a cross-sectional top-view of a surgical lead located in relation to a spinal cord at a leftward position.

Referring to FIG. 13d, the spinal cord is rotated through angle 1330 and positioned leftward by a distance 1329. Path $P_8$ defines a light path from optical element 1208 to reflection point $R_8$ and then to optical element 1209. The length of path $P_8$ is $D_8$ which is less than length $D_5$ but about the same as $D_6$. Optical element 1208 emits light along path $P_8$ and optical element 1209 collects light from path $P_8$ after reflection at point $R_8$ from spinal cord 1220. Light collected by optical element 1209 is detected by photodetector 1204 which produces a photocurrent of $I_8$ in response. $I_8$ is about the same as $I_6$.

An electric field produced by electrodes 1212 and electrodes 1213, stimulates target cells 1219 in the spinal cord 1220. Table 1 indicates the relative levels of electrode stimulation current required based on photocurrent.

Figure 14:
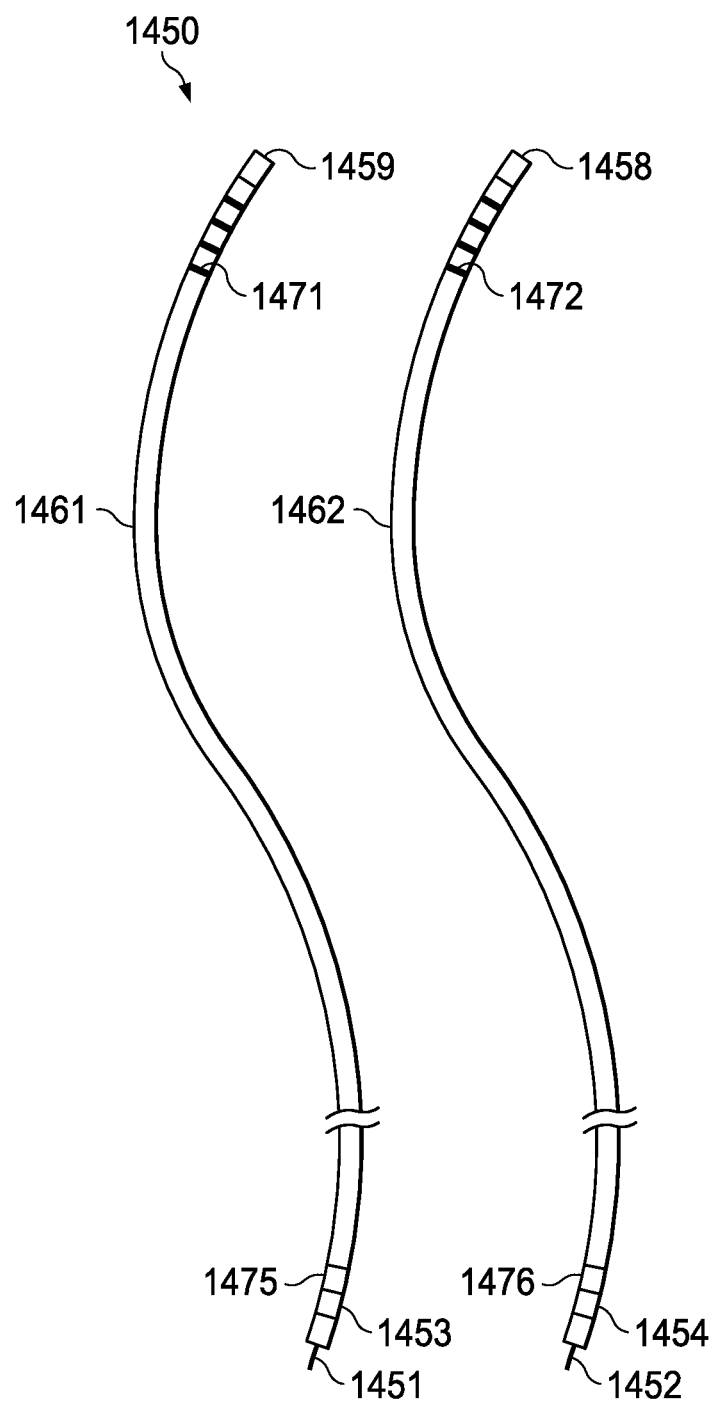
FIG. 14 shows a perspective view of a preferred embodiment of a paired percutaneous lead.

Referring to FIG. 14, alternate embodiment 1450 is shown in which two percutaneous leads are provided. Percutaneous lead 1461 includes optical fiber 1451, optical element 1459, electrodes 1471 and contacts 1475. Optical fiber 1451 is coupled to optical element 1459. Percutaneous lead 1461 also includes electrical wires (not shown). The percutaneous lead terminates in opto-electrical connector 1453.

Percutaneous lead 1462 includes optical fiber 1452, optical element 1458, electrodes 1472 and contacts 1476. Optical fiber 1452 is coupled to optical element 1458. Percutaneous lead 1462 also includes electrical wires (not shown). The percutaneous lead terminates in opto-electrical connector 1454. Percutaneous lead 1461 is identical to percutaneous lead 1462.

Figure 15A:
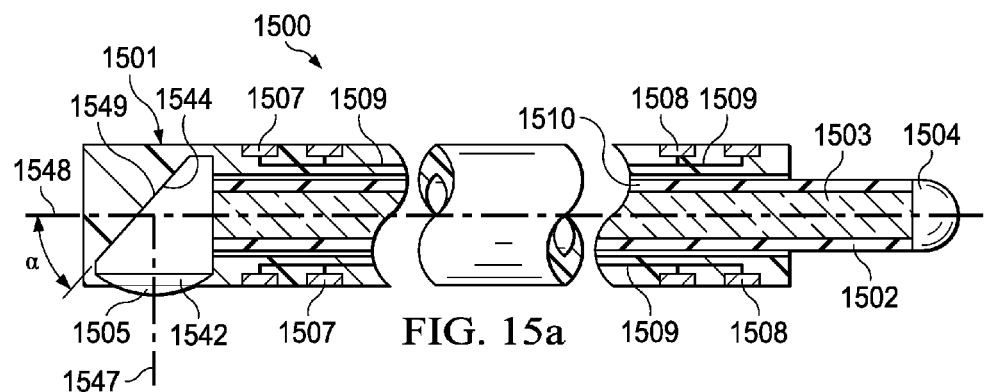
FIG. 15a is a cross-sectional view of an embodiment of a percutaneous lead.

Referring to FIG. 15a, a preferred embodiment of a percutaneous lead is shown. Percutaneous lead 1500 includes lead body 1501 in which an optical fiber 1510 is embedded. Optical fiber 1510 is coupled to collimating lens 1504. Lead body 1501 also includes electrodes 1507 connected by electrical wires 1509 to contacts 1508. Optical fiber 1510 includes a cladding 1502 and a core 1503 co-centered on fiber optic axis 1548. Optical fiber 1510 is coupled to an angled lens assembly 1505.

Angled lens assembly 1505 includes a housing 1549 coupled to optical fiber 1510 and core 1503. Housing 1549 further includes collimating lens 1542 and reflective surface 1544 at an angle α from fiber optic axis 1548. Collimating lens 1542 and reflective surface 1544 are positioned to collimate light along axis 1547. Angle α is preferably in the range of about 30° to about 60°.

Figure 15B:
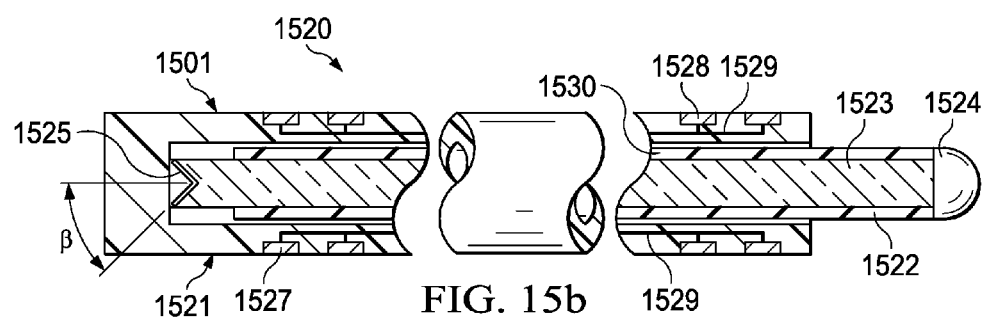
FIG. 15b is a cross-sectional view of a preferred embodiment of a surgical lead.

Referring to FIG. 15b, an alternate embodiment of a percutaneous lead is shown. Percutaneous Lead 1520 includes lead body 1521 in which an optical fiber 1530 is embedded. Optical fiber 1530 is coupled to collimating lens 1524. Lead body 1521 also includes electrodes 1527 connected by electrical wires 1529 to contacts 1528. Optical fiber 1530 includes cladding 1522 and core 1523. Optical fiber 1530 includes negative axicon 1525. For an uncoated negative axicon, angular extent β is less than about 33° for typical glass. The maximum value of β is determined as the complement of the critical angle χ for the optical material in core 1523. The complement of the critical angle is (90°−χ). If the negative axicon has a reflective coating then angular extent 13 is approximately 45°.

Figure 16:
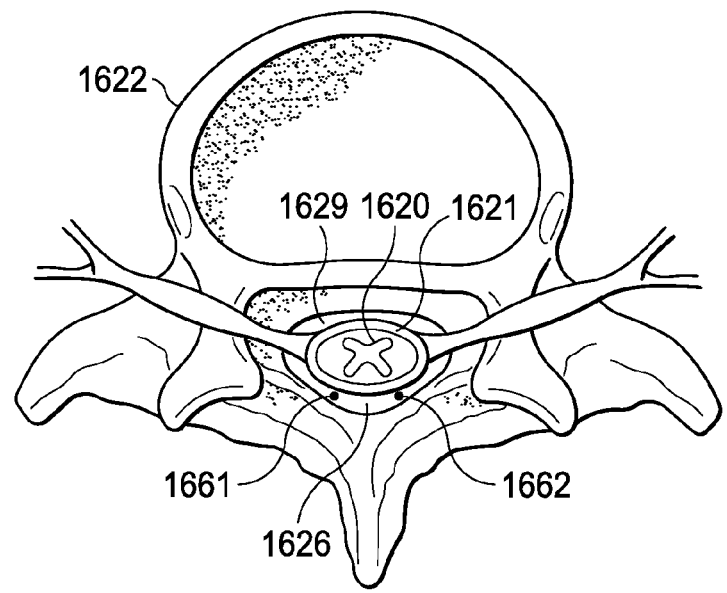
FIG. 16 shows preferred placement of a paired percutaneous surgical lead in a spinal column.

Referring to FIG. 16, a cross-sectional view of vertebra 1622 is shown enclosing spinal cord 1620. Percutaneous lead 1661 and percutaneous lead 1662 are implanted in epidural space 1626 of vertebra 1622 between dura 1621 and the walls of the spinal canal 1629. In a preferred embodiment, the percutaneous leads are implanted side-by-side at a predetermined distance apart, adjacent, and generally parallel to, each other. Placement of percutaneous leads 1661 and 1662 can be accomplished through insertion of the leads through needles placed percutaneously into the epidural space.

Figure 17:
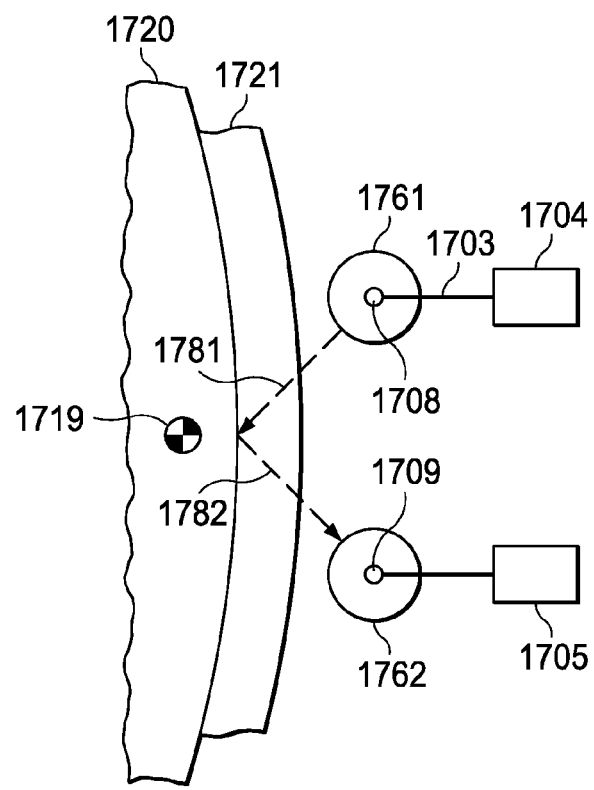
FIG. 17 shows a cross-sectional axial view of a pair of percutaneous leads near a spinal cord.

Referring to FIG. 17, a cross-sectional axial view of the percutaneous leads implanted is shown. Percutaneous lead 1761 includes optical element 1708 and electrodes 1471. Optical element 1708 is coupled to an optical source 1705. Percutaneous lead 1762, also implanted outside dura 1721, includes optical element 1709 and electrodes 1472 where optical element 1709 is coupled to optical detector 1704. Percutaneous leads 1761 and 1762 are positioned within an operational range of target cells 1719 of spinal cord 1720.

In use, a light beam is emitted from optical source 1704, propagates through optical fiber 1703 and exits from optical element 1708 as light beam 1781. Light beam 1781 propagates through the spinal canal, experiences absorption by the dura and the spinal fluid, and is reflected and scattered to create reflected light beam 1782. Reflected light beam 1782 is collected by optical element 1709 and detected by optical source 1705.

Referring to FIGS. 18a-18d, spinal cord 1720 is shown in various positions in the spinal canal in relation to coronal axis 1824 and sagittal axis 1825.

Figure 18A:
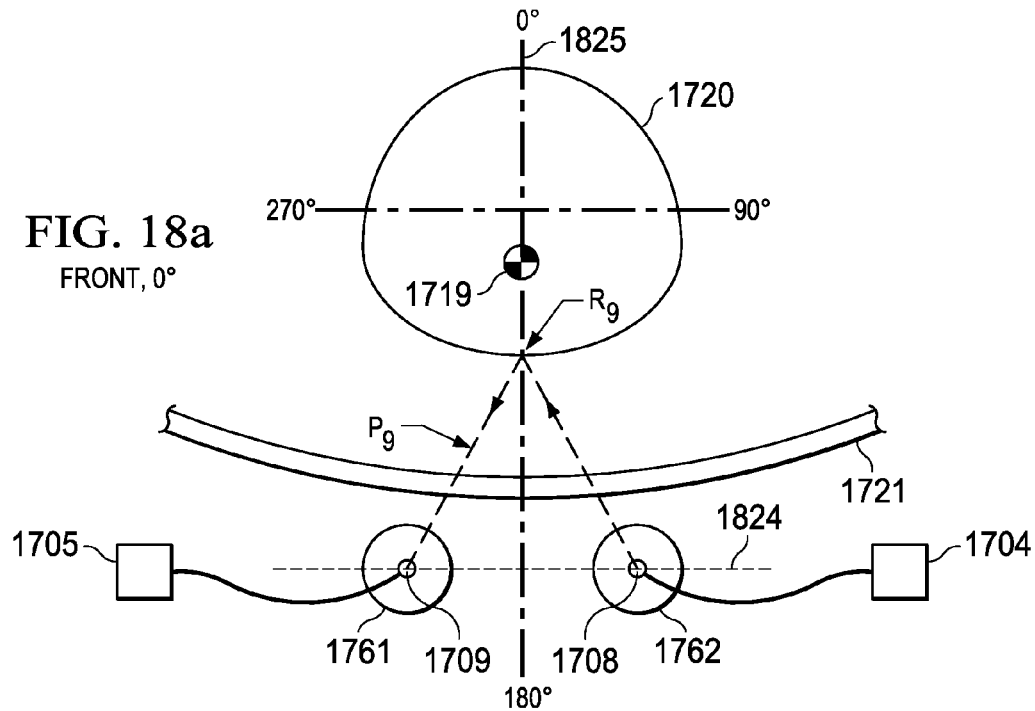
FIG. 18a shows a cross-sectional axial view of a paired percutaneous surgical lead located in relation to a spinal cord at a forward position.

Referring to FIG. 18a, the spinal cord is positioned forward, path $P_9$ defines a light path from optical element 1708 to reflection point $R_9$ and then to optical element 1709. Optical element 1708 emits light, along path $P_9$. Optical element 1709 collects light after reflection from point $R_9$. Light collected by optical element 1709 is detected by optical source 1705 which produces a photocurrent $I_9$ in response.

Figure 18B:
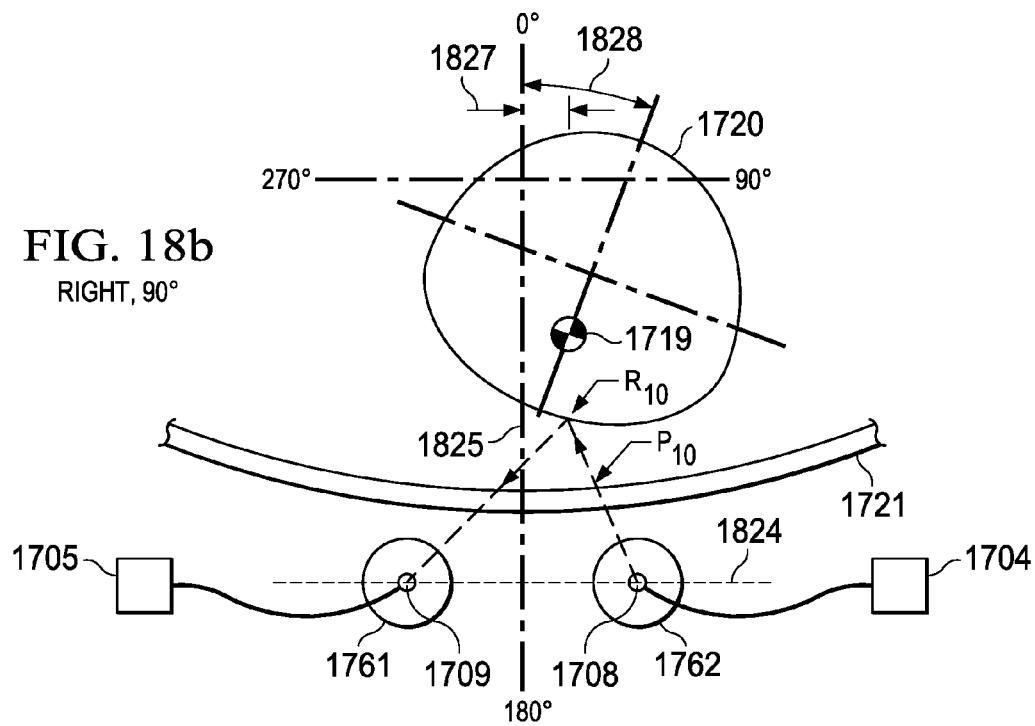
FIG. 18b shows a cross-sectional axial view of a paired percutaneous surgical lead located in relation to a spinal cord at a rightward position.

Referring to FIG. 18b, the spinal cord is rotated through angle 1828 and positioned rightward by a distance 1827 towards 90°. Path $P_{10}$ defines a light path from optical element 1708 to reflection point $R_{10}$ and then to optical element 1709. The length of path $P_{10}$ is less than the length of path $P_9$. Optical element 1708 emits light, including light along path $P_{10}$. Optical element 1709 collects light after reflection at point $R_{10}$. Reflected light collected by optical element 1708 is detected by photodetector 1705 which produces a photocurrent $I_{10}$ in response. $I_{10}$ is greater than $I_9$.

Figure 18C:
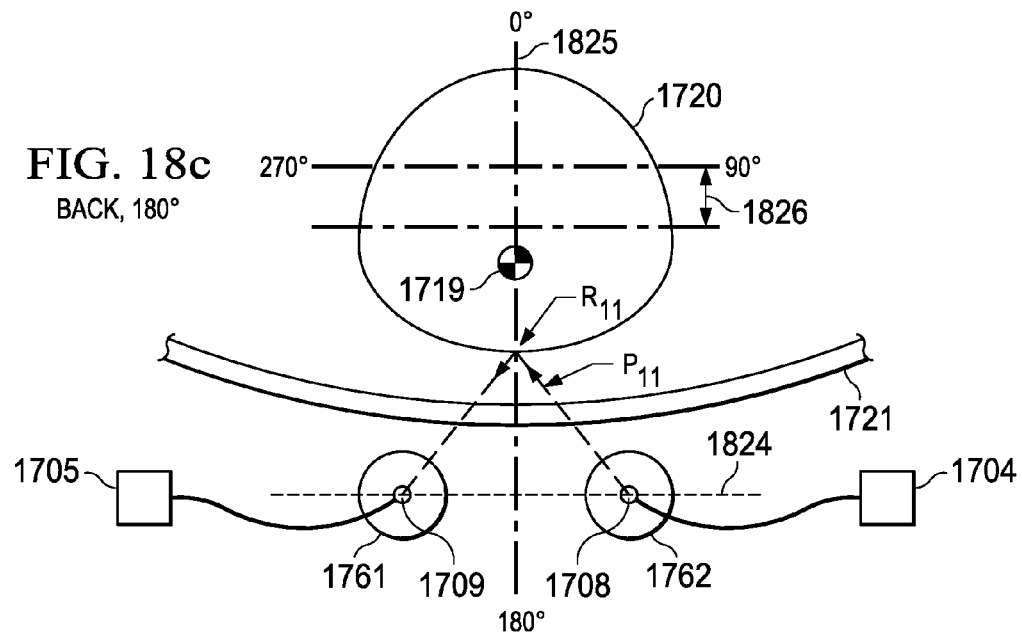
FIG. 18c shows a cross-sectional axial view of a paired percutaneous surgical lead located in relation to a spinal cord at a backward position.

Referring to FIG. 18c, the spinal cord is positioned towards the back and displaced dorsally by a distance 1826. Path $P_{11}$ defines a light path from optical element 1708 to reflection point $R_{11}$ and then to optical element 1709. The length of path $P_{11}$ is shorter than the length of paths $P_9$ or $P_{10}$. Optical element 1708 emits light, including light along path $P_{11}$. Optical element 1709 collects reflected light. Reflected light collected by optical element 1709 is detected by photodetector 1705 which produces a photocurrent $I_{11}$ in response. $I_{11}$ is greater than $I_9$ and $I_{10}$.

Figure 18D:
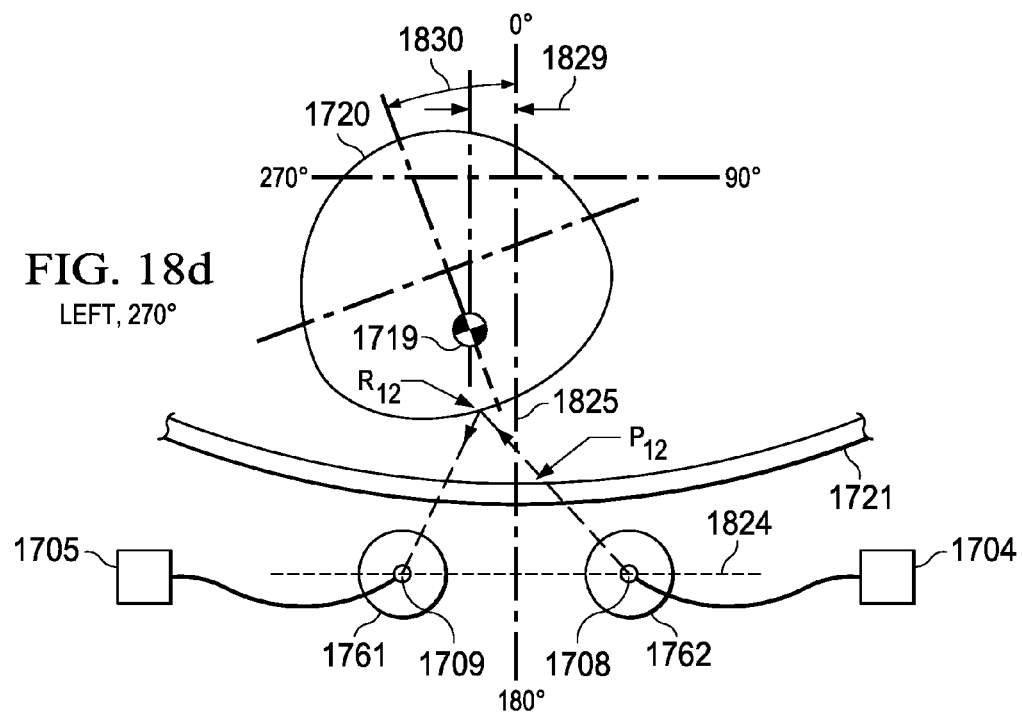
FIG. 18d shows a cross-sectional axial view of a paired percutaneous surgical lead located in relation to a spinal cord at a leftward position.

Referring to FIG. 18d, the spinal cord is rotated through angle 1830 and positioned leftward by a distance 1829 towards 270°. Path $P_{12}$ defines a light path from optical element 1708 to reflection point $R_{12}$ and then to optical element 1709. The length of path $P_{12}$ is less than length of path $P_9$ but about the same as the length of path $P_{10}$. Optical element 1708 emits light, including light along path $P_{12}$. Optical element 1709 collects reflected light, including light from path $P_{12}$. Reflected light collected by optical element 1709 is detected by photodetector 1705 which produces a photocurrent $I_{12}$ in response. $I_{12}$ is about the same amplitude as $I_{10}$.

The relative electrode stimulation amplitudes for various photocurrents are summarized by Table 1.

Figure 19:
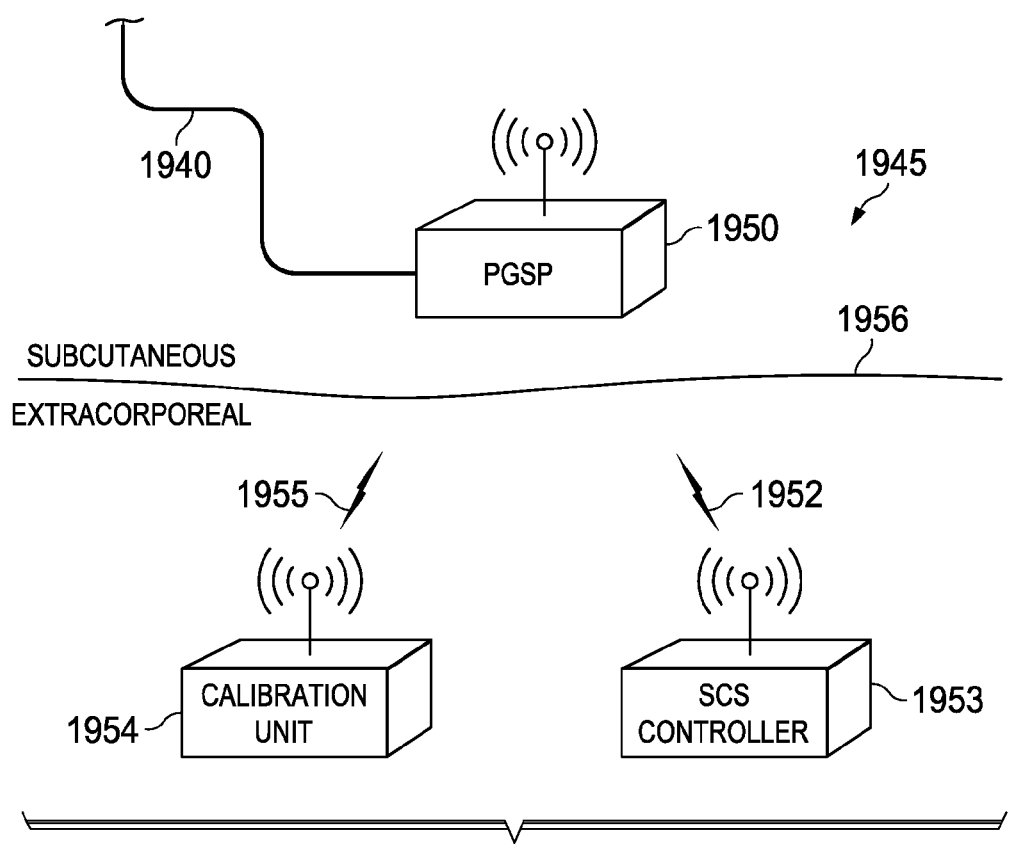
FIG. 19 is a block diagram of a preferred embodiment of a stimulator system.

Referring to FIG. 19, a preferred embodiment of a stimulator system is shown. Stimulator system 1945 includes pulse generator and signal processor (PGSP unit) 1950 is connected to stimulator lead assembly 1940. PGSP unit 1950 provides power to the electrodes in stimulator lead assembly 1940 and houses electronic and electro-optical components of the system. Stimulator lead assembly 1940 connects the stimulator electrodes of each stimulator lead to a controllable current source. Stimulator lead assembly 1940 further connects at least one infrared emitter to at least one optical fiber through a first fiber optical connector and at least one photodetector to at least one optical fiber through additional fiber optic connectors.

In a preferred embodiment PGSP unit 1950 is installed subcutaneously in a patient and stimulator lead assembly 1940 includes a percutaneous lead or a surgical lead. In an alternate embodiment, PGSP unit 1950 is outside the host patient's body and stimulator lead assembly includes the percutaneous leads.

PGSP unit 1950 gathers and processes photodetector signals and makes adjustments to the stimulator electrode current (or voltage) based on the photodetector signals. PGSP unit 1950 is connected by wireless communication link 1952 across skin boundary 1956 to SCS controller 1953. The SCS controller is configured to allow percutaneous activation of and adjustments to stimulator system 1945. PGSP unit 1950 is also connected by wireless communication link 1955 to calibration and programming unit 1954. Calibration and programming unit 1954 is programmed to accept patient input and transmit the patient input to PGSP 1950 during calibration. In an alternate embodiment, calibration and programming unit 1954 is incorporated into SCS controller 1953.

PGSP unit 1950 is preferably powered by batteries. In an alternate embodiment, PGSP unit 1950 derives power from capacitive or inductive coupling devices. Wireless communication links 1952 or 1955 may further serve as a means of providing electrical charge for the batteries or capacitive devices of PGSP unit 1950.

Figure 20:
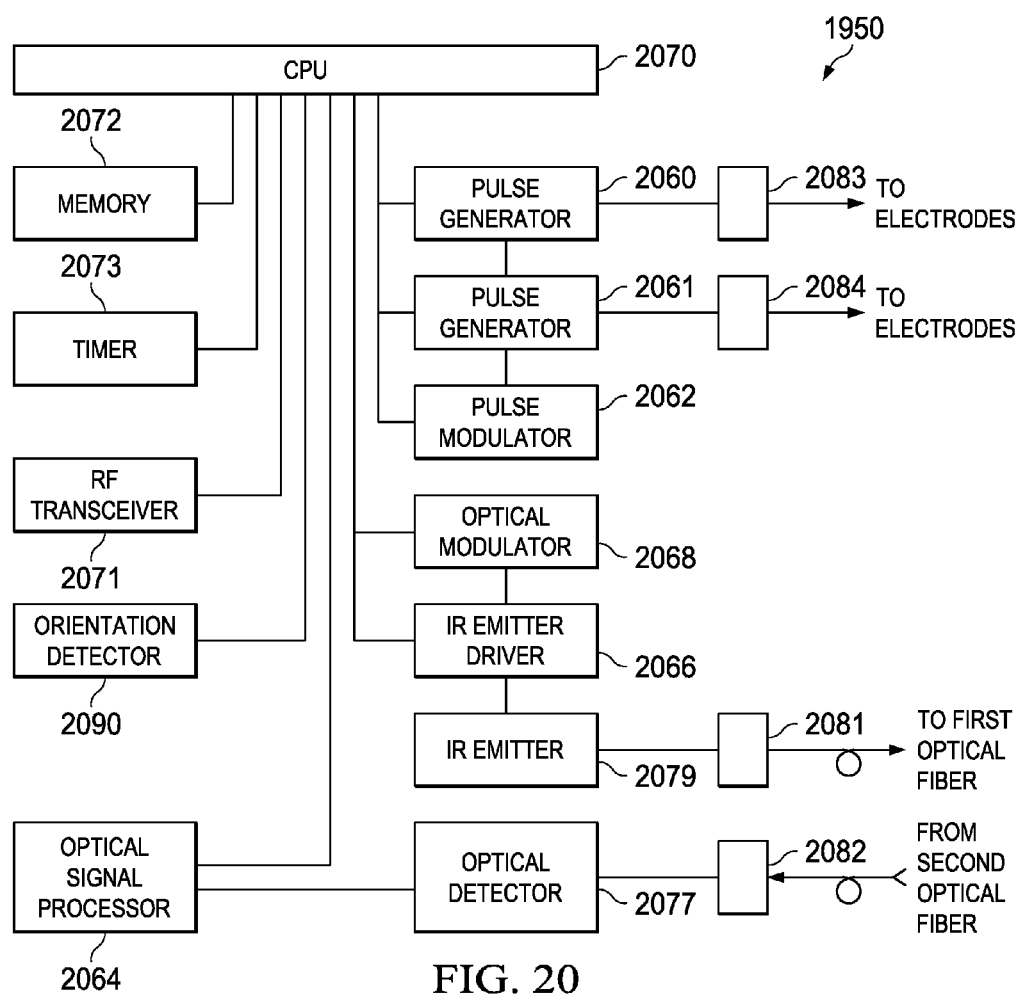
FIG. 20 is a block diagram of a preferred embodiment of a pulse generator and signal processing unit.

Referring to FIG. 20, a block diagram of PGSP unit 1950 is shown. PGSP unit 1950 includes CPU 2070 having onboard memory 2072 and hardware timer 2073. In a preferred embodiment, the memory includes two data buffers which are used as "stacks." The hardware timer includes a timer register. CPU 2070 is connected to pulse modulator 2062, pulse generator 2060, and pulse generator 2061. Pulse modulator 2062 is connected to pulse generators 2060 and 2061 which are further connected to a stimulator lead through lead connectors 2083 and 2084, respectively. CPU 2070 is also operatively connected to optical modulator 2068 and optical signal processor 2064. Optical modulator 2068 is connected to emitter driver 2066. Emitter driver 2066 is connected to IR emitter 2079 and drives IR emitter 2079. IR emitter 2079 includes fiber optic connector 2081 to effectively couple IR emitter 2079 to a first optical fiber which is further connected to a first distal optical element in a surgical lead or percutaneous lead assembly.

Optical detector 2077 is connected to fiber optical connector 2082 to effectively couple optical detector 2077 to a second optical fiber which is further connected to a second distal optical element in a surgical lead or percutaneous lead assembly. Optical detector 2077 translates incoming light pulses from the optical fiber into electrical signals which are processed by optical signal processor 2064.

In a preferred embodiment, the photodetector is similar to that of Part No. OP501 from Optek Technology.

CPU 2070 is connected to optical signal processor 2064. Optical signal processor 2064 is connected to optical detector 2077 and receives an optical signal from the photodetector and filters the optical signal. Optical signal processor 2064 may include a synchronized gated detection (e.g., lock-in amplifier type) function or other demodulation function to improve the signal to noise ratio of the detected light.

CPU 2070 is connected to optical modulator 2068. Emitter driver 2066 is connected to both optical modulator 2068 and CPU 2070.

In operation, CPU 2070 activates optical modulator 2068 which generates a waveform and transmits the waveform to the emitter driver 2066. The emitter driver then causes IR emitter 2079 to launch a light pulse with the waveform into the first optical fiber.

The optical waveform may take several forms. For example, the pulse width of the optical waveform may have a low duty cycle to minimize power consumption. A single optical pulse may occur for multiple electrode stimulation pulses. The optical waveform may include frequency, phase or amplitude modulation. Typical wavelength of the IR light from the IR emitter is in a range from 800 nm to 870 nm. Typical output intensity of the IR emitter is 1 to 2 mW and a suitable part is Part No. VSMY1859 from Vishay Intertechnology, Inc.

Pulse generator 2060 is connected to electrodes in stimulator lead assembly 1940 through lead connector 2083. In order to generate a pulse to the electrodes, CPU 2070 consults a calibration table stored in onboard memory 2072 to determine pulse width PW, pulse frequency Pf and pulse amplitudes for the electrodes, respectively. The pulse width and frequency are transmitted to pulse modulator 2062 which creates a modified square wave signal. The modified square wave signal is passed to pulse generator 2060. CPU 2070 passes the amplitudes for the electrodes to pulse generator 2060 in digital form. Pulse generator 2060 then regulates the peak current or voltage of the modified square waves according to the pulse amplitudes and transmits them to the electrodes through lead connector 2083. CPU 2070 is in transcutaneous communications, via RF transceiver 2071, with calibration and programming unit 1954 and SCS controller 1953. Pulse generator 2060 and pulse modulator 2062 may collectively be composed of a digital-to-analog converter with associated current or voltage sources.

Pulse generator 2061 is connected to electrodes in stimulator lead assembly 1940 through lead connector 2084. In order to generate a pulse to the electrodes, CPU 2070 consults a calibration table stored in onboard memory 2072 to determine pulse width PW, pulse frequency Pf and pulse amplitudes for the electrodes, respectively. The pulse width and frequency are transmitted to pulse modulator 2062 which creates a modified square wave signal and passes it to pulse generator 2061. CPU 2070 passes the amplitudes for the electrodes to pulse generator 2061 in digital form. Pulse generator 2061 then regulates the peak amplitude of the modified square waves according to the pulse amplitudes and transmits them to electrodes through lead connector 2084. CPU 2070 is in transcutaneous communications, via RF transceiver 2071, with calibration and programming unit 1954 and SCS controller 1953. Pulse generator 2061 and pulse modulator 2062 may collectively be composed of a digital-to-analog converter with associated current or voltage sources.

The modified square wave has an amplitude and duration (or width). Pulse widths varying from 20 to 1000 microseconds have been shown to be effective. The frequency of the pulse waveforms between 20 and 10,000 hertz have been shown to be effective. The output amplitude is preferably from 0 (zero) to +/−20 mA or 0 (zero) to +/−10 V but may vary beyond those ranges according to patient sensitivity.

PGSP unit 1950 also includes an orientation detector 2090 for determining the physical orientation of the patient including roll, pitch and yaw coordinates. Preferably, the orientation detector can distinguish lack of motion in the patient for a predefined period of time. A suitable component for the orientation detector is one of part numbers UM6-LT and MiniMU-9 orientation sensors from Polulu Corporation.

In a preferred embodiment, orientation detector 2090 is installed or affixed to the PGSP. In a preferred embodiment, the PGSP is installed so that the orientation detector roll axis coincides with the patient's longitudinal axis (intersection of sagittal and coronal planes), the pitch axis coincides with a first transverse axis (intersection of transverse and coronal planes), and the yaw axis coincides with a second transverse axis (intersection of transverse and sagittal planes).

Figure 21:
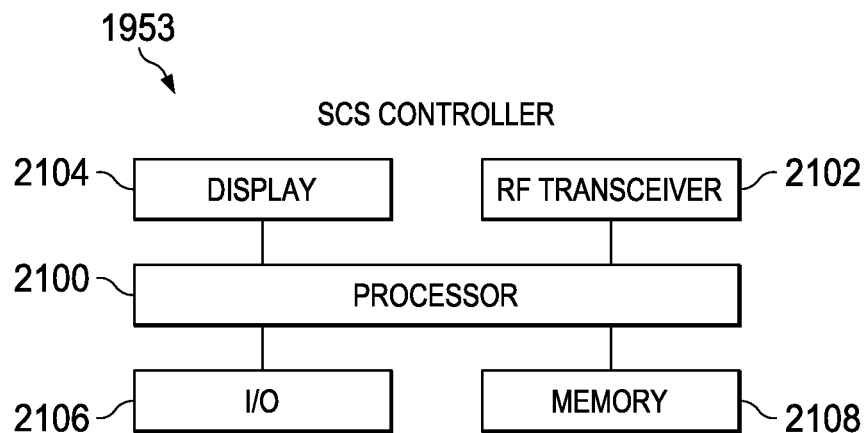
FIG. 21 is a block diagram of the components of a preferred embodiment of an SCS controller.

Referring to FIG. 21, SCS controller 1953 is shown. SCS controller 1953 includes processor 2100 connected to RF transceiver 2102, to display 2104, to input/output device 2106 and to memory 2108. In the preferred embodiment, display 2104 is a low power liquid crystal display adapted to show the current operational state of the system. I/O device 2106 is a simple push button contact array which is constantly monitored by processor 2100. In the preferred embodiment, RF transceiver 2102 is a low power transmitter/receiver combination.

Figure 22:
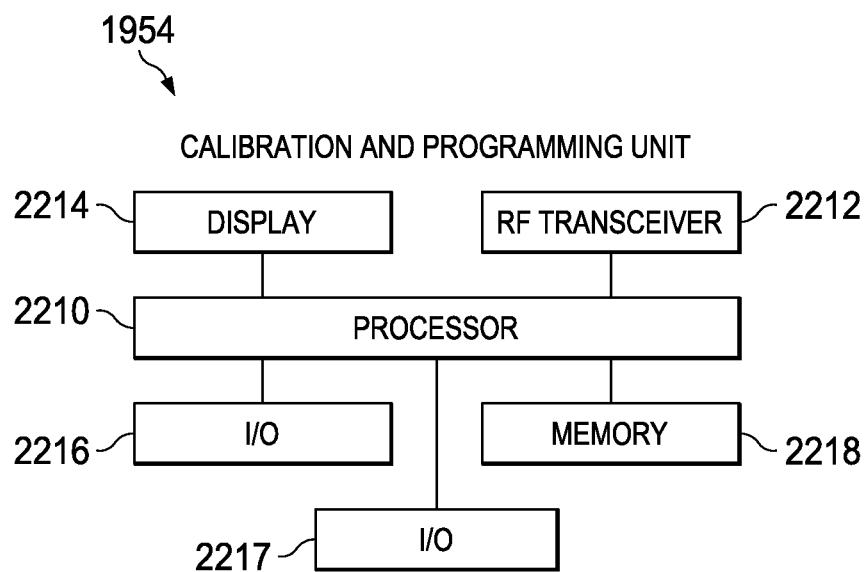
FIG. 22 is a block diagram of the components of a preferred embodiment of a calibration and programming unit.

Referring to FIG. 22, calibration and programming unit 1954 is described. Calibration and programming unit 1954 includes processor 2210 connected to onboard memory 2218, to input/output devices 2216 and 2217, to RF transceiver 2212 and to display 2214. Display 2214, in the preferred embodiment, is a low power liquid crystal display. Input/output device 2216 and input/output device 2217 are simple push button switches monitored continuously by the processor. RF transceiver 2212 is a low power transmitter/receiver combination.

Figure 23:
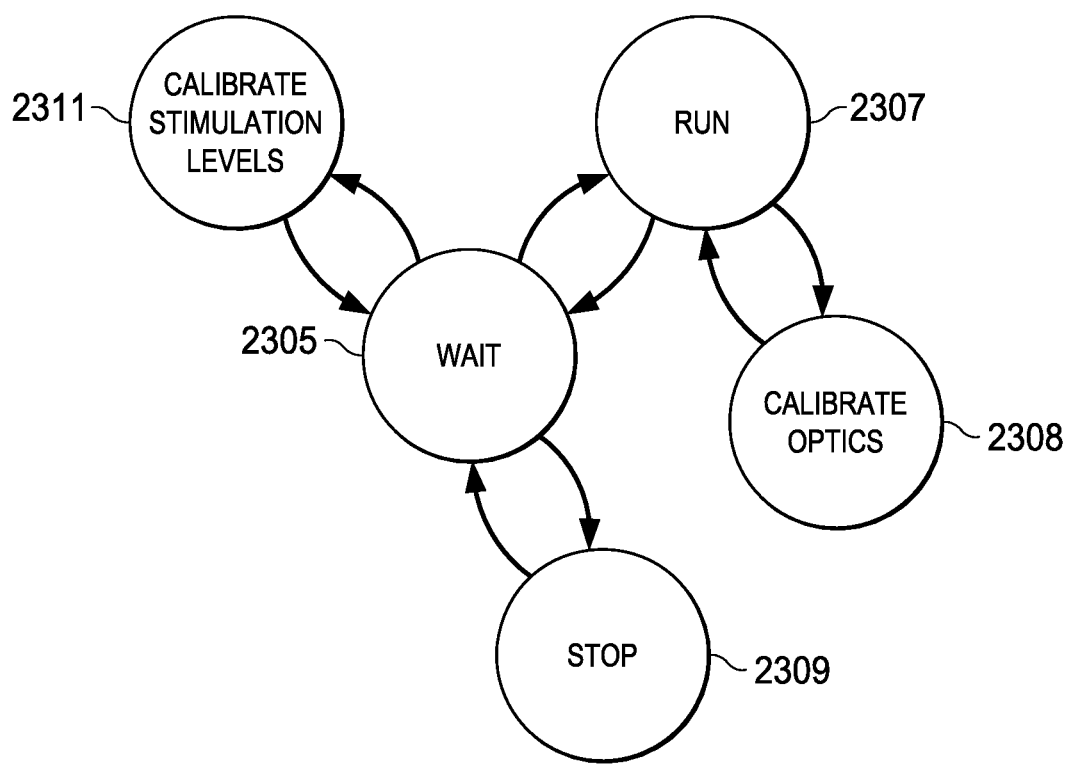
FIG. 23 is a state diagram of a preferred embodiment of a stimulator control system.

Referring to FIG. 23, the various states of the SCS controller in operation will be described. At wait state 2305, SCS controller 1953 enters a waiting posture and continually polls the I/O device and responds to system interrupt signals, for example, a timer interrupt to enter the "run" state. Upon receipt of a "run" signal from the I/O device, the processor enters "run" state 2307 and transmits a "run" signal to the RF transceiver. The RF transceiver then transmits the "run" signal to PGSP 1950 for further action, for example, executing a run cycle method. After transmission, the processor returns to wait state 2305.

While in "run" state 2307, if the patient is determined to be at rest for a predetermined period of time, then the SCS controller enters the "calibrate optics" state 2308 and the optical source is recalibrated. After the recalibration of the optical source is complete or if the patient begins to move, the SCS controller returns to "run" state 2307.

If a "stop" signal is received from the I/O device, the processor passes a "stop" signal to the RF transceiver, which in turn sends the "stop" signal to PGSP 1950. The PGSP unit then enters stop state 2309. The processor then returns to wait state 2305. If the "stop" signal includes a directive to turn off power, then power to the PGSP unit is shut down in the stop state and no electrode stimulation current is applied to the host patient.

If a "calibrate" signal is received from I/O device 2106, processor 2100 transmits a "calibrate" signal to RF transceiver 2102, which in turn sends the "calibrate" signal to PGSP 1950. The system enters "calibrate stimulation" state 2311 in which parasthesia levels are optimized in certain patient positions and stimulation current calibrated for the host patient. Processor 2100 returns to wait state 2305 after calibration is complete.

FIG. 24 shows calibration table 2440 for the stimulation system. The table is stored in memory and includes optimal electrode settings for each patient position. In a preferred embodiment, column 2442 includes four patient positions: forward (prone)—0°, right lateral—90°, back (supine)—180°, and left lateral—270°. Each row in calibration table 2440 is associated with one of the patient positions. In an alternate embodiment, additional physical positions are included.

In the preferred embodiment, column 2444 stores values for the roll, pitch and yaw orientation for the patient. Column 2446 stores values for the current measured for each photodetector. Column 2448 stores values for the electrode stimulation pulse amplitude which produces the optimal paresthesia (or stimulation) in that patient position. Column 2450 stores values for the electrode stimulation pulse width. Column 2452 stores values for the electrode stimulation pulse frequency.

FIG. 25 shows an alternate preferred embodiment of a calibration table 2500. In a preferred embodiment, column 2510 provides a row index. Column 2511 provides a location to store patient positions comparing to the row index. Each row in calibration table 2500 is associated with one of the row indices. Column 2512 stores values for the minimum photocurrent provided by the photodetectors at the patient positions. Column 2513 stores values for the corresponding maximum photocurrent delivered by the photodetectors. Column 2514 stores values for the minimum stimulation current amplitude for the right electrodes. Column 2515 stores values for the maximum stimulation current for the right electrodes. Column 2516 stores the values for the stimulation current amplitudes for the left electrodes. Column 2517 stores values for the maximum stimulation current for the left electrodes.

The maximum and minimum stimulation current amplitudes are provided to set the stimulator in a range of current amplitudes between a minimum, where no response is felt, and a maximum where the stimulation is noxious. The maximum and minimum values are determined during electrode pulse stimulation calibration, as will be further described.

Figure 26:
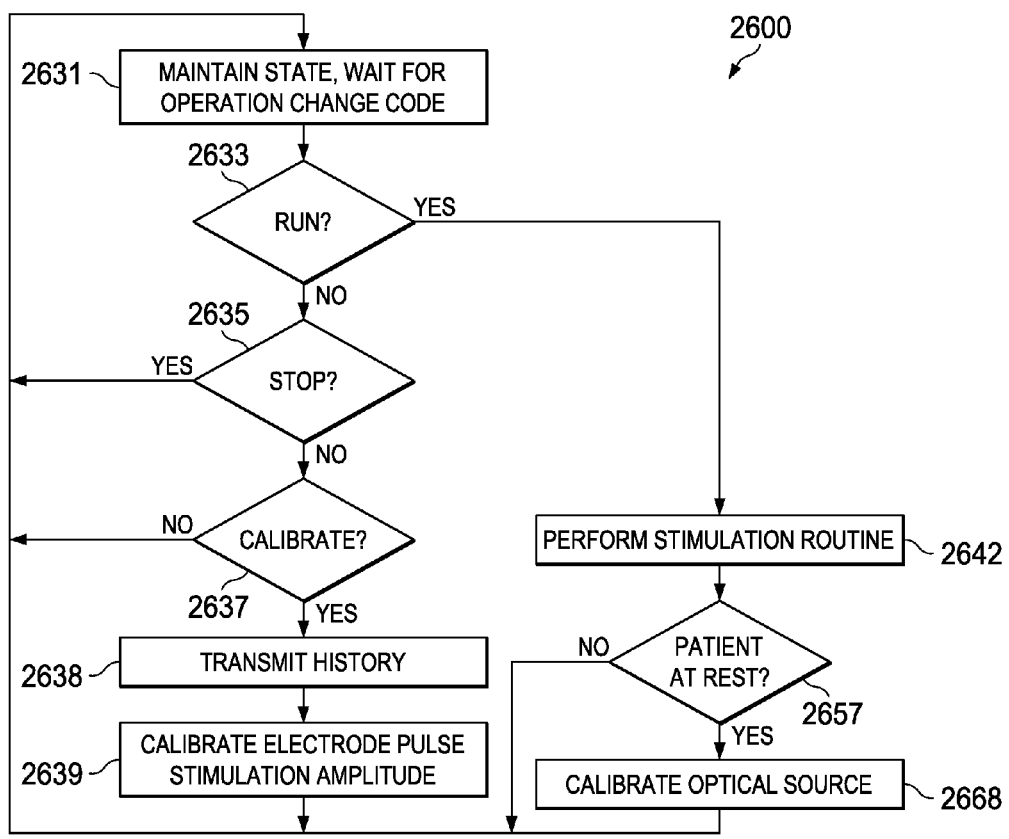
FIG. 26 is a flow chart of a method of operation for a stimulator system.

Referring to FIG. 26, an embodiment of a method of operation of the stimulation system is described. In a preferred embodiment, method 2600 is implemented by a computer program which is resident in onboard memory 2072 of CPU 2070 of PGSP 1950.

At step 2631, RF transceiver 2071 is polled for a change of operation code signal received from SCS controller 1953. The system maintains its current operational state until a change of operation code is received. In a preferred embodiment, a change of operation code signal is initiated by an interrupt generated by a hardware timer. In an alternate preferred embodiment, the change of operation code can be initiated by a button press.

At step 2633, if operation change code "run" is received, the method moves to step 2642. At step 2642, a stimulation routine is performed to adjust the electrode stimulation current for the patient based on photocurrent measurements. This step is further described below.

At step 2657, the CPU determines if the patient is at rest. In this step, the physical orientation of the patient is monitored by reading changes in values of roll, pitch and yaw that have occurred during a predetermined time interval. If the values are unchanged for a minimum arbitrarily defined duration, then the patient is assumed to be at rest and the method moves to step 2668. At step 2668, the optical source is calibrated based on the patient's position, as will be described more fully below. The method then returns to step 2631.

If, at step 2657, the patient is determined not to be at rest, then the method returns to step 2631.

If, at step 2633, the operation change code is not "run", then the method moves to step 2635. At step 2635, the CPU determines if the operation change code is "stop". If the change code is "stop", then the method returns to step 2631.

If, at step 2635, the operation change code is not "stop", then the method moves to step 2637. At step 2637, the CPU determines if the operation change code is "calibrate." If, at step 2637, the operation change code is not "calibrate", then the method returns to step 2631.

If, at step 2637, the operation change code is "calibrate", then the method moves to step 2638. At step 2638, the CPU transmits historical data to the calibration and programming unit where it is stored. The historical data comprises a copy of the current calibration table, a value of optical source current, orientation sensor calibration data and a time series of electrode stimulation settings as they were performed by the stimulation routine since the previous calibration. At step 2639, the CPU performs a calibration of stimulation current levels for the patient as will be described more fully below. The method then returns to step 2631.

Figure 27A:
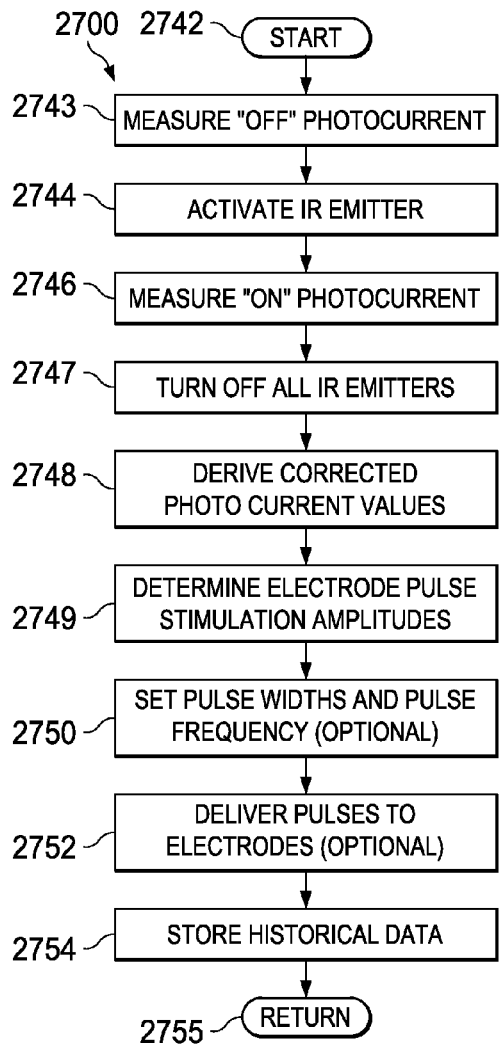
FIG. 27*a* is a flow chart of a method of performing a stimulation routine.

Referring to FIG. 27a, method 2700 for performing the stimulation routine 2642 is described. The method starts at step 2742. At step 2743, a photocurrent value is measured for each photodetector with the IR emitter in the "off" state. At step 2744, CPU 2070 activates optical modulator 2068, which in turn activates emitter driver 2066 to generate an optical pulse from the IR emitter. At step 2746, photocurrent values for each photodetector are measured with the IR emitter in the "on" state. At step 2747, the IR emitter is turned off. At step 2748, corrected photocurrent values are derived by subtracting the "off" photocurrent value from the "on" photocurrent value for each IR detector. In a preferred embodiment, this step employs the equation:

$$PD_{corr} = PD_{meas} - PD_{dark} \quad \text{(Eq. 3)}$$

where $PD_{meas}$ is the "on" photocurrent value, $PD_{dark}$ is the "off" photocurrent value and $PD_{corr}$ is a corrected photocurrent value. The corrected photocurrent values are stored in memory.

At step 2749, the CPU determines the electrode stimulation pulse amplitudes. In one preferred embodiment, the electrode stimulation pulse amplitudes are interpolated from the calibration table based on the photodetector current. For example, referring to FIG. 24, if the corrected photocurrent value of $PD_{corr}$ has a value between $PD_2$ and $PD_3$, then a stimulation amplitude A is determined from a linear interpolation according to:

$$A = A_2 + \frac{\Delta A}{\Delta PD}(PD_{corr} - PD_2) \quad \text{(Eq. 4)}$$

where $\Delta A=(A_3-A_2)$ and $\Delta PD=(PD_3-PD_2)$.

In another preferred embodiment, a spline interpolation is used. Other interpolation methods as known in the art can be employed.

At step 2750, the CPU optionally sets values of electrode stimulation pulse width and electrode stimulation pulse frequency. In the preferred embodiment, electrode stimulation pulse width and electrode stimulation pulse frequency are constant. In another embodiment, electrode stimulation amplitude is constant and electrode stimulation pulse width is varied as a function of photocurrent. In another embodiment, electrode stimulation amplitude is constant and electrode stimulation pulse frequency is varied as a function of photocurrent.

At step 2752, the CPU optionally activates the pulse modulator to create a waveform which is impressed on the pulse trains sent to the electrodes and then activates the pulse generator to deliver the pulse trains. At step 2754, the CPU stores the corrected photocurrent values, the electrode stimulation pulse amplitudes, the electrode stimulation pulse widths and the electrode stimulation pulse frequencies in memory. At step 2755, the method returns.

Figure 27B:
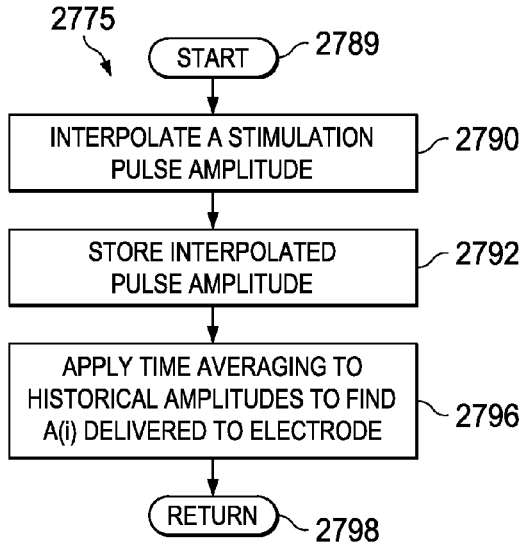
FIG. 27*b* is a flow chart of an alternate method of performing a stimulation routine.

Referring to FIG. 27*b*, alternate method 2775 of determining electrode stimulation pulse amplitudes of step 2749, is described. The method starts at step 2789. At step 2790, the CPU interpolates an electrode stimulation pulse amplitude from the calibration table. At step 2792, the interpolated electrode stimulation pulse amplitude is stored in memory in a time series of interpolated stimulation amplitude values. The time series of interpolated simulation amplitude values is a historical record of the stimulation amplitudes applied to the electrodes over a predetermined past period of time. At step 2796, the CPU performs a moving average over the time series of interpolated stimulation amplitude values to determine an electrode pulse amplitude. The calculation of the electrode pulse amplitude is made using the following equation:

$$A_{ave} = \frac{w_k \cdot A_k + w_{k-1} \cdot A_{k-1} + w_{k-2} \cdot A_{k-2} + \ldots}{w_k + w_{k-1} + w_{k-2} + \ldots}, \quad \text{(Eq. 5)}$$

where $A_{ave}$ is the pulse amplitude applied to the electrode, $w_k$ is a predetermined weight for value $A_k$, in the time series of stimulation amplitude values, at the current time k, value $A_{k-1}$ at the previous time (k−1) and so forth for earlier times (k−2), (k−3), . . . , etc. For example, the predetermined weights are predefined to fall off exponentially where $w_k=w_0 e^{-ak}$ and the sum in Eq. 5 is capped to include N terms. At step 2798, the method returns.

Figure 28A:
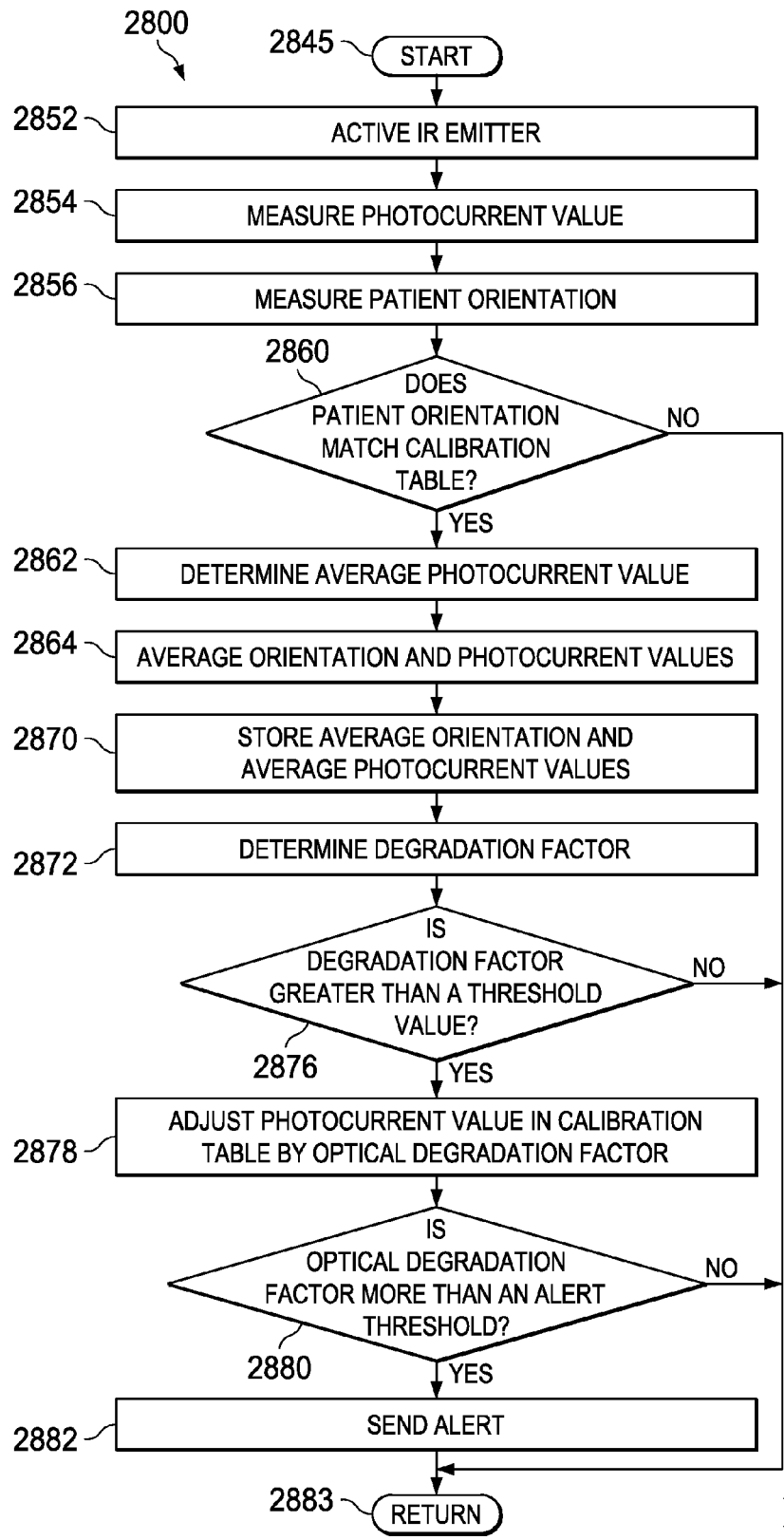
FIG. 28*a* is a flow chart of a method for calibrating an optical source.

Referring to FIG. 28*a*, method 2800 to calibrate the optical source of step 2668 is described. When the optical source degrades, generally the photocurrent levels will decrease for a given patient orientation. Degradation of the optical source occurs for many reasons, for example, changes in the position of the surgical lead, growth of scar tissue, and fracturing of optical components and fibers, among other causes. The optical calibration method detects and corrects for long term degradations in performance of the optical components of the system.

At step 2845, the method starts. At step 2852, the IR emitter is turned "on." As a result, light from the IR emitter is reflected from the spinal cord and received by the photodetector. At step 2854, the resulting photocurrent is measured. At step 2856, the patient orientation is measured. In a preferred embodiment, the patient orientation is measured by polling the orientation detector for absolute roll, pitch and yaw coordinates. At step 2860, the roll, pitch and yaw coordinates are then compared to those recorded in the calibration table. If a match is determined within a predefined confidence interval, such as ±10%, then that patient position is reported as the instant patient position. Then the method moves to step 2862. If a match is not determined within the confidence interval, then the method returns at step 2883. At step 2862, the instant photocurrent is measured and stored. At step 2864, the average photocurrent is calculated for a predetermined period of time past.

At step 2864, the average photo current value for the instant patent position is determined. The average photocurrent value is determined for a predetermined past period of time for that patient position and reported as the average photocurrent value. At step 2870, the average orientation and the average photocurrent values are stored.

At step 2872, an optical degradation factor is determined. In a preferred embodiment, the optical degradation is a ratio between the average photocurrent value and the instant photocurrent value.

At step 2876, the optical degradation factor is compared to a threshold value. If at step 2876, the optical degradation factor is not more than the threshold value, then the method returns at step 2883. If, at step 2876, the optical degradation factor is more than the threshold value, then the method moves to step 2878. At step 2878, the photocurrent value in the calibration table for the instant patient position is multiplied by the optical degradation factor.

If, at step 2880, the optical degradation factor is greater than an alert threshold, then an alert is sent at step 2882. For example, the alert can be a periodic audible sound or a displayed message on an LCD or LED display included with the SCS controller. The method then returns at step 2883. If, at step 2880, the optical degradation factor is not greater than an alert threshold, the method returns at step 2883.

Figure 28B:
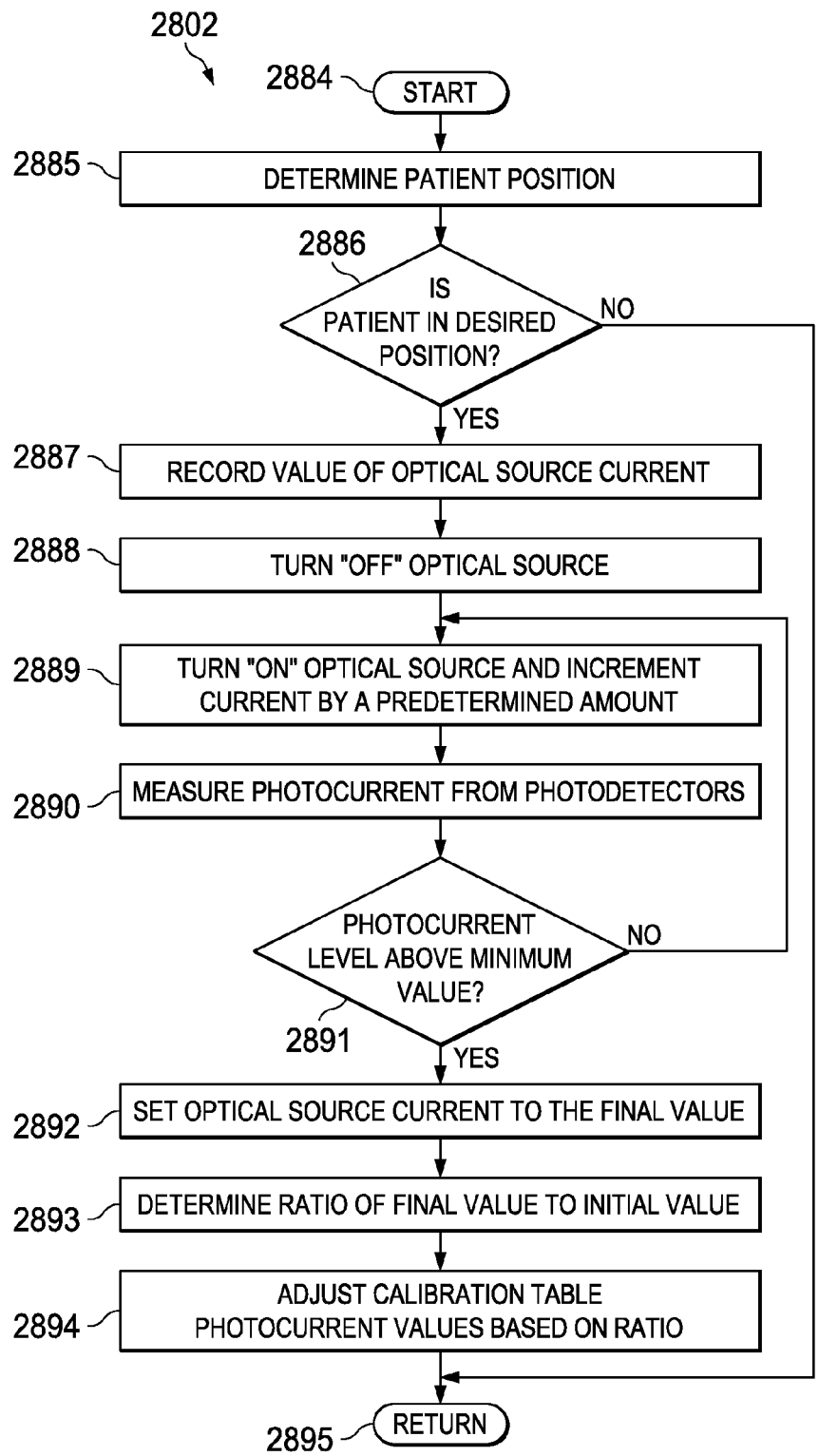
FIG. 28*b* is a flow chart of an alternate method for calibrating an optical source.

Referring to FIG. 28*b*, an alternate method of calibrating the optical source is described. According to method 2802, the optical source is only calibrated if the patient is in a desired position. In the preferred embodiment, the desired position is the prone position. In the prone position, the spinal cord is farthest from the optical emitter and optical collector of the stimulation system. Hence, the optical source current determines the minimum detectable photocurrent level. In a preferred embodiment, method 2802 is called in step 3089 during calibration of the optical source.

Method 2802 starts at step 2884. At step 2885, patient position is determined. The patient position is determined by referencing the patient position in the calibration table which corresponds to the running average of corrected photocurrent value. In an alternate embodiment, the patient position is determined by polling the orientation detector. At step 2886, the patient position is compared to a desired patient position.

If, at step 2886, the patient is not in the desired position, then the optical source is not calibrated and the method returns at step 2895. If, at step 2886, the patient is in the desired position, then the method moves to step 2887.

At step 2887, the optical source current is stored. At step 2888, the source current is turned "off." At step 2889, the optical source current is turned "on" and the current to it is increased by a predetermined amount.

At step 2890, the photocurrent from the photodetectors is measured. At step 2891, the photocurrent is compared to a predetermined minimum value. In a preferred embodiment, the predetermined minimum value is between 1.5 and 4.0 times the current value measured from the photodetectors when the optical source is "off."

If the photocurrent level is not greater than the minimum value, then the method returns to step 2889.

If the photocurrent is greater than the predetermined minimum value, then the method continues to step 2892. At step 2892, a final optical source current is set.

At step 2893, a ratio of the final optical source current to the initial optical source current is determined. At step 2894, the photocurrent values in the calibration table are adjusted based on the ratio. In a preferred embodiment, all of the calibrated photocurrent values in the calibration table are multiplied by the ratio.

Then, at step 2895, the method returns.

Figure 29A:
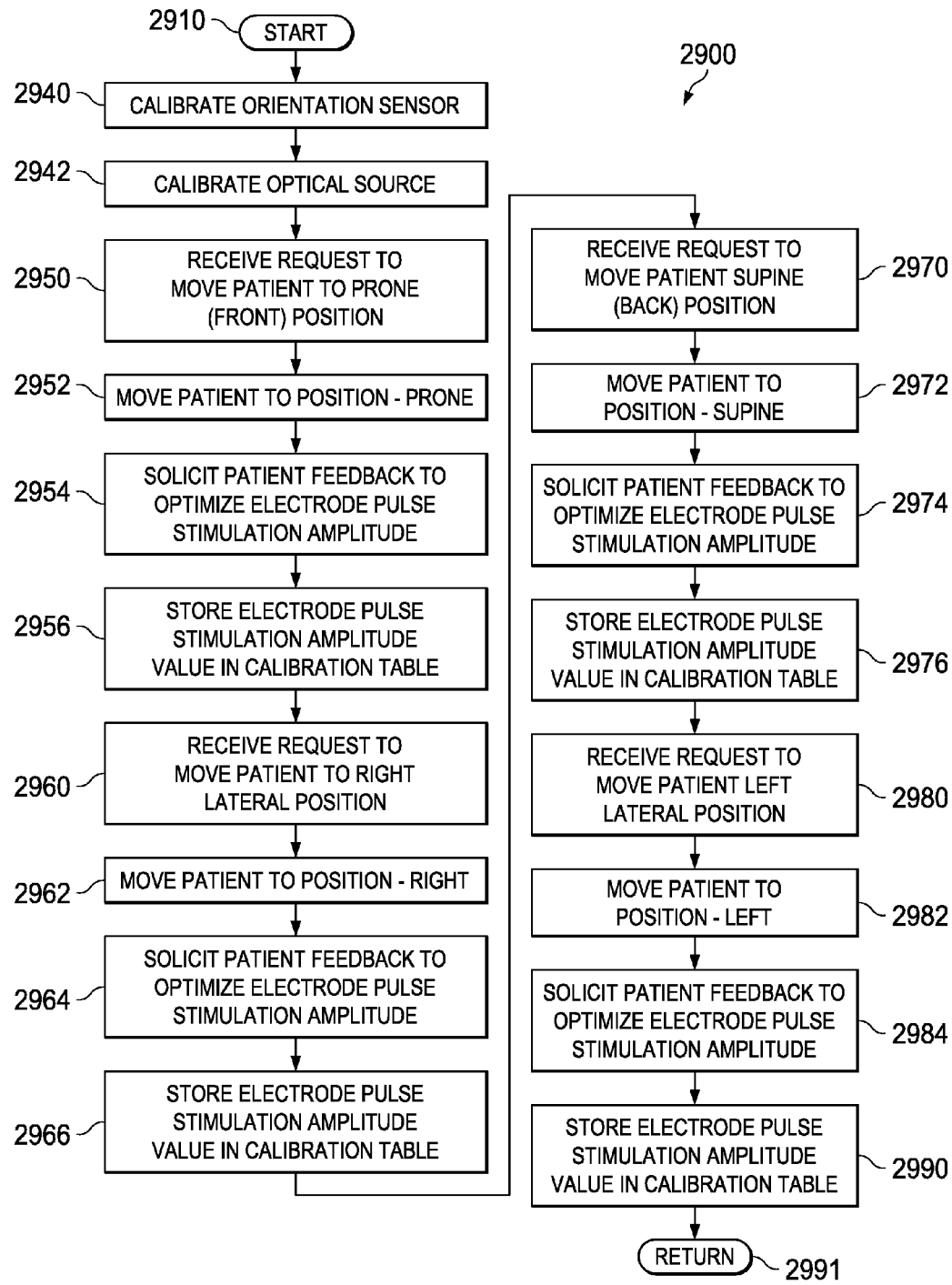
FIG. 29*a* is a flow chart of a method of calibration of electrode pulse simulation amplitude.

Referring to FIG. 29a, method 2900 for calibrating electrode pulse stimulation amplitude, at step 2639, is described.

At step 2910, the method starts. At step 2940, the orientation sensor is calibrated. In a preferred embodiment, the orientation sensor is calibrated to read a roll of 0°, a pitch of 0° and a yaw of 0° when the patient is in a known position. At step 2942, the optical source is calibrated as has been described.

At step 2950, the RF transceiver receives a signal indicative of a request to move the patient to a prone position and passes the request to the CPU. At step 2952, the patient is physically positioned in a prone position. At step 2954, electrode pulse stimulation amplitude is adjusted based on patient feedback to optimize the level of paresthesia experienced by the patient while in the prone position. This position is used to set the right and left maximum electrode pulse amplitudes. At step 2956, the photocurrent level and corresponding electrode stimulation pulse amplitude for the position is stored in the calibration table.

At step 2960, the RF transceiver receives a signal indicative of a request to move the patient to a right lateral position and passes it to the CPU. At step 2962, the patient is positioned in a right lateral position. At step 2964, electrode pulse stimulation amplitude is adjusted based on patient feedback to optimize the level of paresthesia experienced by the patient while in the right lateral position. At step 2966, the photocurrent level and corresponding electrode stimulation pulse amplitude for the position is stored in the calibration table.

At step 2970, the RF transceiver receives a signal indicative of a request to move the patient to a supine position and passes it to the CPU. At step 2972, the patient is positioned in a supine position. At step 2974, electrode pulse stimulation amplitude is adjusted based on patient feedback to optimize the level of paresthesia experienced by the patient while in the supine position. This position is used to set the right and left minimum electrode pulse amplitudes. At step 2976, the photocurrent level and corresponding electrode stimulation pulse amplitude for the position is stored in the calibration table.

At step 2980, the RF transceiver receives a signal indicative of a request to move the patient to a left lateral position and passes it to the CPU. At step 2982, the patient is positioned in a left lateral position. At step 2984, electrode pulse stimulation amplitude is adjusted based on patient feedback to optimize the level of paresthesia experienced by the patient while in the left lateral position.

At step 2990, the photocurrent level and corresponding electrode stimulation pulse amplitude for the position is stored in the calibration table.

In other embodiments, the order in which the patient is positioned may be changed. Also, additional and/or different patient positions may be added.

At step 2991, the method returns.

Figure 29B:
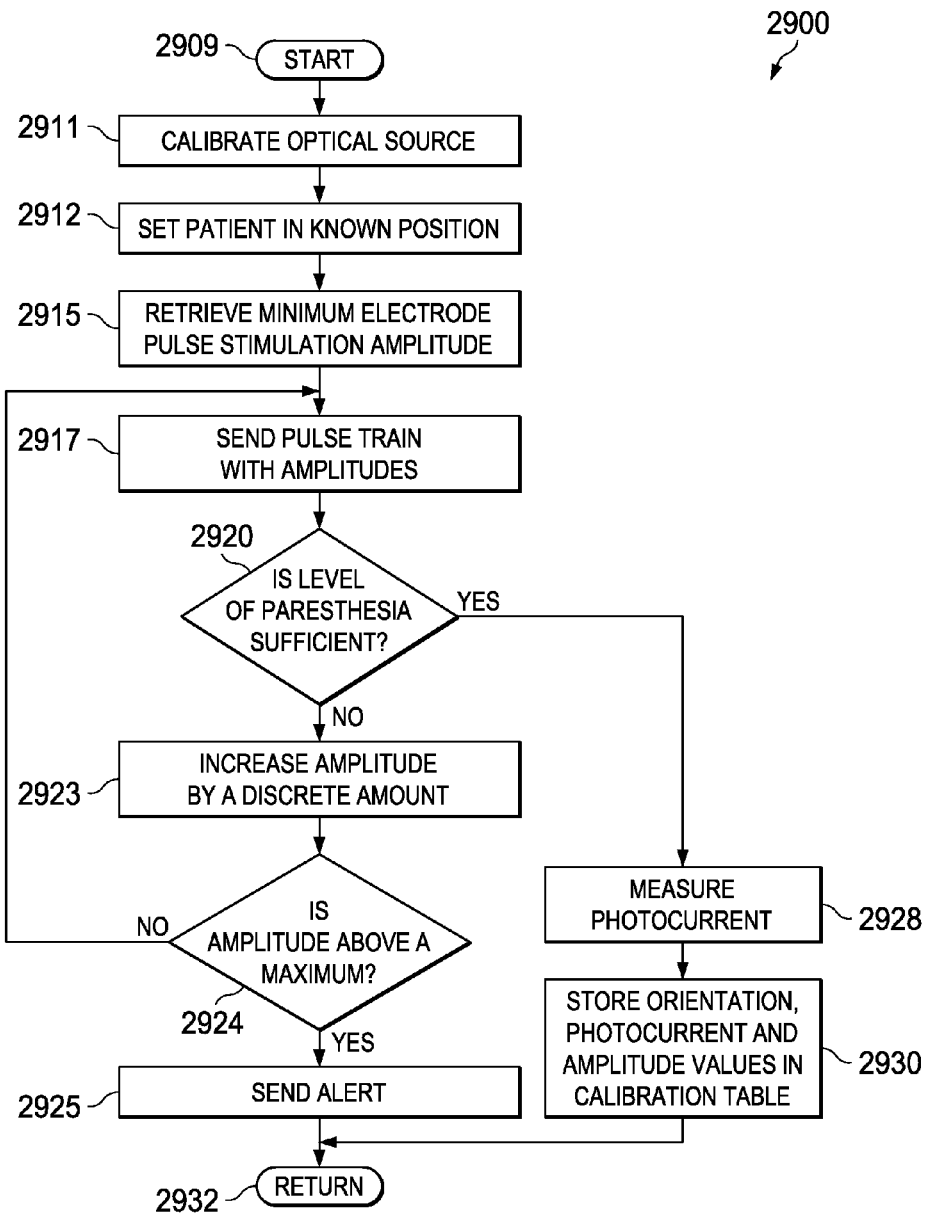
FIG. 29*b* is a flow chart of an alternate method of calibration of electrode pulse simulation amplitude.

Referring to FIG. 29b, alternate method 2900 for calibrating electrode pulse stimulation amplitudes, at step 2639, is described. At step 2909, the method starts.

At step 2911, the optical source is calibrated as has been described.

At step 2912, the patient is physically placed in a known position. In a preferred embodiment, the known position corresponds to one of the 0°, 90°, 180° or 270° positions, previously described.

At step 2915, the minimum electrode pulse stimulation amplitude for the given patient position is obtained from the calibration table. In this embodiment, the calibration table 2500 may be employed.

At step 2917, the pulse generator is directed by the CPU to send a train of pulses to the electrodes at the minimum electrode stimulation pulse amplitude. At step 2920, paresthesia feedback is solicited from the patient in order to determine if the level of paresthesia is optimal.

If the level of paresthesia is not optimal, then the method moves to step 2923. At step 2923, the processor increases the electrode stimulation pulse amplitude by a discrete amount. If, at step 2924, the electrode pulse stimulation amplitude reaches a maximum level, step 2925 is performed. At step 2925, an alert is sent to the physician. The alert may take the form of an audible sound or a text display. The method then returns at step 2932. If, at step 2924, the electrode pulse stimulation amplitude has not reached a maximum level, the method returns to step 2917.

If, at step 2920, the level of paresthesia is optimal, then the method moves to step 2928. At step 2928, the optical signal processor measures the photocurrent for the photodetector. At step 2930, the amplitude levels are stored in the calibration table. At step 2932, the method returns.

Figure 30A:
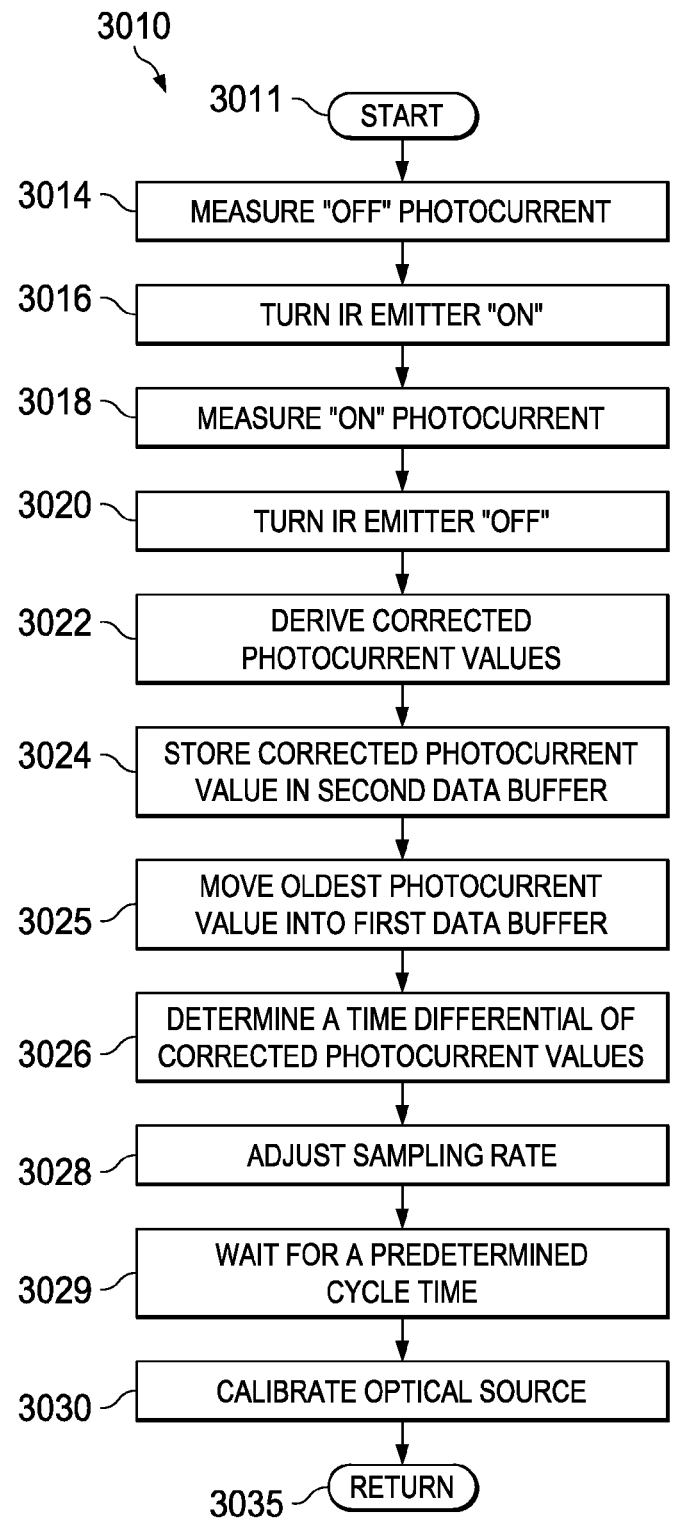
FIG. 30*a* is a flow chart of an alternate method of performing a stimulation routine.

Referring to FIG. 30a, a preferred embodiment of method 3010 for performing a stimulation routine, step 2642, is described. The method starts at step 3011.

At step 3014, an "off" photocurrent is measured from the photodetector while the IR emitter is turned off. At step 3016, the IR emitter is turned "on." At step 3018, an "on" photocurrent is measured. At step 3020, the IR emitter is turned off.

At step 3022, a corrected photocurrent value is calculated by subtracting the "off" photocurrent value from the "on" photocurrent value. At step 3024, the corrected photocurrent value is stored in the second data buffer. At step 3025, the oldest photocurrent value from the second data buffer is shifted into the first data buffer when the second data buffer is full.

At step 3026, a time differential value of photocurrent is determined. The time differential value is determined in order to "smooth" transitions from one stimulation value to another. In a preferred embodiment, the values of photocurrent in the first data buffer are averaged. The values of photocurrent stored in the second data buffer are averaged. Then a difference is taken between the first average value and the second average value according to the equation:

$$\text{DIFF} = |PD(t_1) - PD(t_0)|, \quad \text{(Eq. 6)}$$

where DIFF is the time differential value, PD(t₀) is the first average value and PD(t₁) is the second average value.

At step 3028, a sampling rate is adjusted based on the time differential value. A method for the adjusting the sampling rate is described in more detail below.

At step 3029, the system delays for a predetermined cycle time. The cycle time is adjusted to increase or decrease the sampling rate to conserve power when the patient is at rest.

At step 3030, the optical source is calibrated, as has been described.

At step 3035, the method returns.

Figure 30B:
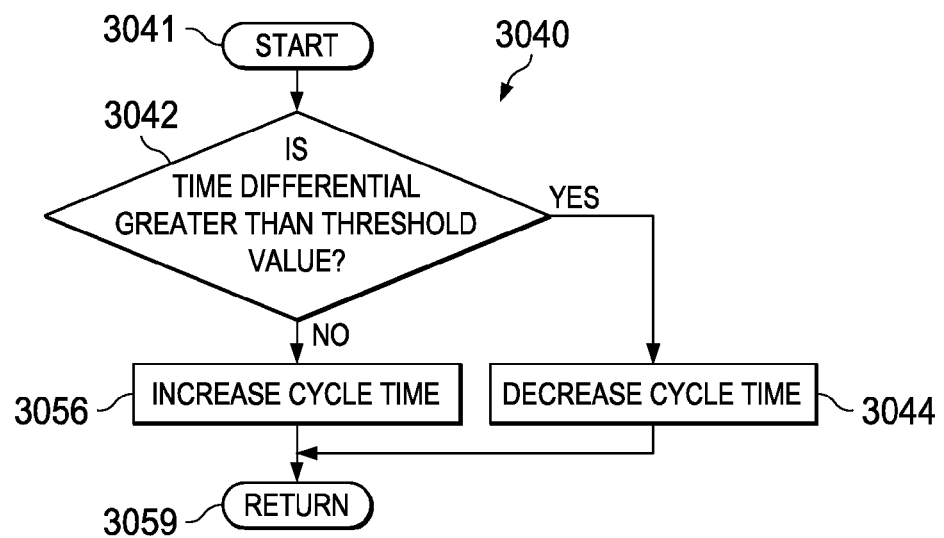
FIG. 30*b* is a flow chart of a method of adjusting cycle time and electrode pulse stimulation current.

Referring to FIG. 30*b*, method 3040 for adjusting the cycle time is described. The cycle time is increased when the patient is at rest in order to reduce power consumption. In a preferred embodiment, method 3040 is called at step 3028 of method 3010.

Method 3040 starts at step 3041. At step 3042, a time differential value is compared to the threshold value for patient movement to determine if the patient is moving or at rest. If the time differential value is greater than the threshold value then it is assumed that the patient is moving and the method moves to step 3044. At step 3044, the cycle time is decreased so that the position of the patient is more frequently determined when the patient is active.

If the time differential value is less than the threshold value then it is assumed that the patient is at rest and the method moves to step 3056. At step 3056, the cycle time is increased by a predetermined cycle time increment, up to the maximum cycle time. The cycle time is increased so that the position of the patient is less frequently determined when it is changing less, when the patient is at rest. The method then returns at step 3059.

Figure 30C:
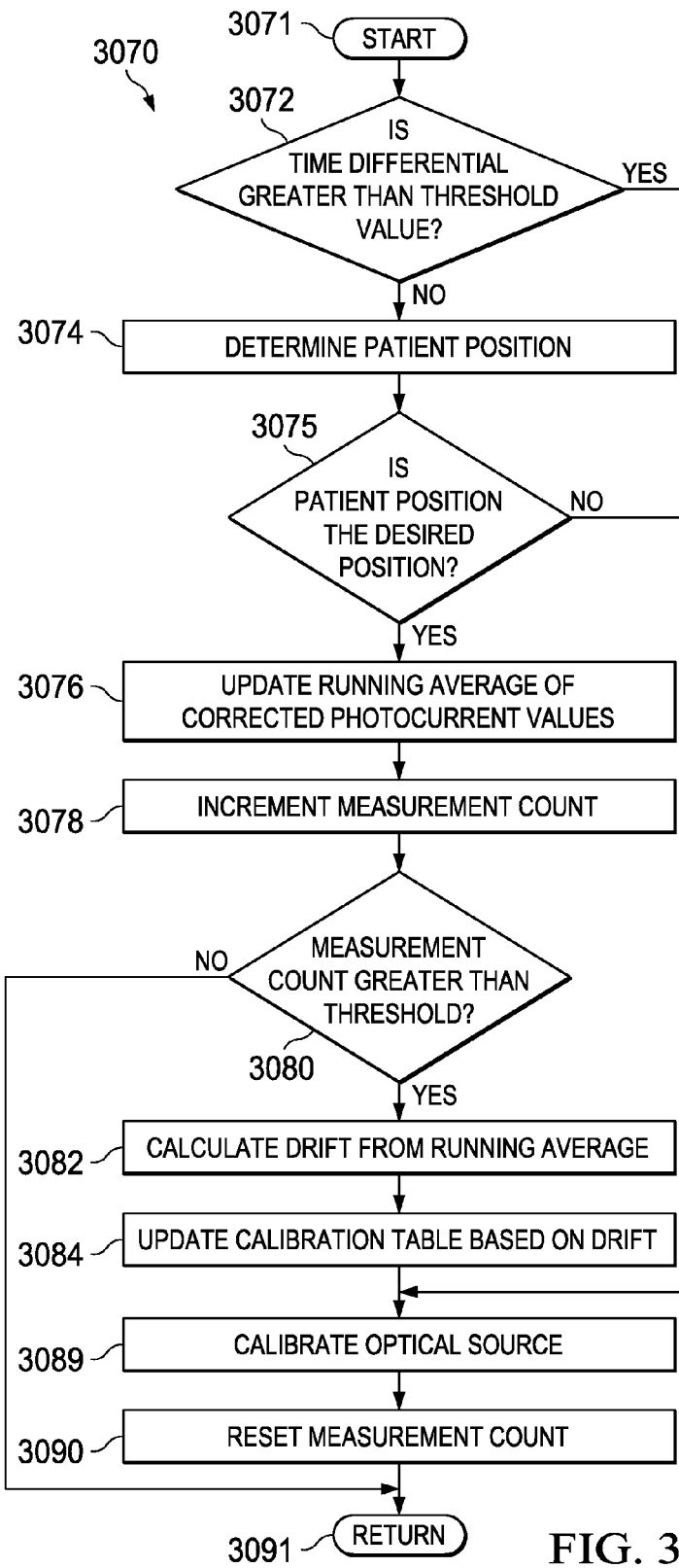
FIG. 30*c* is a flow chart of a method to accelerate calibration of an optical source.

Referring to FIG. 30*c*, method 3070 is described for accelerating calibration of the optical source. In a preferred embodiment, method 3070 is called in step 3030 of method 3010.

The method starts at step 3071. At step 3072, the time differential value is compared to a predetermined threshold value. If the time differential value is greater than a predetermined threshold value, then the patient is assumed to be moving. The method moves to step 3089.

If the time differential value is less than or equal to the predetermined threshold value, then the patient is assumed to be still. The method then moves to step 3074. At step 3074, the patient position is determined. A running average of corrected photocurrent values, PD$_{avg}$, is compared to the photocurrent values in the calibration table to determine the patient position. In an alternate embodiment, the patient position is determined by reading the orientation detector.

At step 3075, the patient position is compared to a desired position. For example, the supine position or prone position. If the patient is not in the desired position, then the optical source is not calibrated and the method continues at step 3089. If the patient is in the desired position, then the method continues with step 3076.

At step 3076, the running average of corrected photocurrent values is updated based on the most recent corrected photocurrent value measured for the patient position. At step 3078, the measurement count is incremented.

At step 3080, the measurement count is compared to a predetermined count threshold. Step 3080 ensures that the running average has been averaged over a sufficiently large number of measurements to accurately calibrate the optical source and to ensure the patient has been motionless for an adequate period. If at step 3080, the measurement count does not exceed the predetermined count threshold, then an optical calibration cycle is not performed. The method then returns at step 3091. If at step 3080, the measurement count exceeds or equals the calibration threshold then the method moves to step 3082.

At step 3082, a drift amount is calculated from the running average. For example, the drift amount is calculated according to:

$$DRIFT = PD_{avg}(S) - \left(\frac{P_{min}(S) + P_{max}(S)}{2}\right) \quad \text{(Eq. 7)}$$

where S is the row index of the calibration table of the patient position, P$_{min}$(S) is from the calibration table in row S and P$_{max}$(S) is from the calibration table in row S.

At step 3084, the calibration table is updated. In a preferred embodiment, the sum of DRIFT and P$_{min}$(S) replaces P$_{min}$(S) in the calibration table and the sum of DRIFT and P$_{max}$(S) replaces P$_{max}$(S) in the calibration table.

At step 3089, the optical source is calibrated as has been described. At step 3090, the measurement count is reset to zero. The method returns at step 3091.

While the present disclosure has been described in terms of specific embodiments thereof, it will be understood in view of the present disclosure, that numerous variations upon the disclosure are now enabled to those skilled in the art, which variations yet reside within the scope of the present teaching. Accordingly, the disclosure is to be broadly construed and limited only by the scope and spirit of the claims now appended hereto.

The invention claimed is:

1. A lead connection apparatus for a stimulator controller comprising:
   a lead connector, adapted to be attached to the stimulator controller, comprising a cavity;
   the cavity having a side surface and an end surface;
   a lead having a first end and a second end;
   the second end positioned in the cavity;
   a set of electrodes attached to the first end;
   a set of electrical contacts, attached to the second end, and electrically connected to the set of electrodes;
   an optical fiber, embedded in the lead;
   an optical element, attached to the optical fiber at the first end;
   a first optical coupler, attached to the optical fiber at the second end;
   a set of spring connectors, attached to the cavity, in contact with the set of electrical contacts;
   a second optical coupler, attached to the cavity;
   an electro-optical device optically coupled through the first optical coupler and the second optical coupler to the optical fiber; and,
   the spring connectors disposed only on one side of the cavity and implanted on and extending from the epoxy header adjacent the cavity.

2. The lead connection apparatus of claim 1 wherein the first optical coupler is a collimating lens.

3. The lead connection apparatus of claim 1 wherein the second optical coupler is a transparent window.

4. The lead connection apparatus of claim 1 wherein:
   the first optical coupler further comprises a first polished ferrule;
   the second optical coupler further comprises a second polished ferrule; and,
   the first polished ferrule and the second polished ferrule form a fiber optic coupling.

5. The lead connection apparatus of claim 1 wherein the first optical coupler and the second optical coupler form an angle-polished fiber optic coupling.

6. The lead connection apparatus of claim 1 wherein the lead is a surgical lead.

7. The lead connection apparatus of claim 1 wherein the lead is a percutaneous lead.

8. The lead connection apparatus of claim 1 further comprising:
- the lead connection apparatus forming part of a system comprising the stimulator controller;
- the stimulator controller adapted to apply an electrode current to the lead;
- the stimulator controller adapted to detect a photocurrent level of the optical fiber;
- the stimulator controller adapted to store a calibration table in a memory; and,
- the stimulator controller adapted to determine the electrode current from the photocurrent level based on the calibration table.

9. The lead connection apparatus of claim 1:
wherein the first optical coupler is a collimating lens;
wherein the second optical coupler is a near-infrared (NIR) transparent window;
and further comprising:
- the lead inserted into the cavity until the collimating lens is adjacent the NIR transparent window;
- the cavity comprising a first cavity and a second cavity;
- the second cavity connecting to the first cavity and terminating in the NIR transparent window;
- the NIR transparent window forming a hermetic barrier between the second cavity and the electro-optical device;
- the electro-optical device situated behind the NIR transparent window; and,
- the electro-optical device being one of an optical emitter and an optical detector.

10. The lead connection apparatus of claim 9 wherein the NIR transparent window is flat.

11. The lead connection apparatus of claim 9:
wherein the collimating lens is an optical fiber with a polished end; and,
wherein the NIR transparent window is a lens.

* * * * *

UNITED STATES PATENT AND TRADEMARK OFFICE
CERTIFICATE OF CORRECTION

PATENT NO. : 9,550,063 B2  
APPLICATION NO. : 14/336796  
DATED : January 24, 2017  
INVENTOR(S) : Erich W. Wolf, II It is certified that error appears in the above-identified patent and that said Letters Patent is hereby corrected as shown below:

In the Specification

Column 11, Line 10: Delete "13" and replace with "β".

Signed and Sealed this  
Second Day of May, 2017

Michelle K. Lee  
*Director of the United States Patent and Trademark Office*